(12) United States Patent
Zolla-Pazner et al.

(10) Patent No.: US 6,241,986 B1
(45) Date of Patent: Jun. 5, 2001

(54) HUMAN MONOCLONAL ANTIBODIES TO THE CD4-BINDING DOMAIN OF HIV, USES THEREOF AND SYNERGISTIC NEUTRALIZATION OF HIV

(75) Inventors: Susan Zolla-Pazner, New York; Miroslaw K. Gorny, Forest Hills; Sylwia Karwowska, Maspeth; Aby Buchbinder, Great Neck, all of NY (US)

(73) Assignee: New York University, New York, NY (US)

(*) Notice: Subject to any disclaimer, the term of this patent is extended or adjusted under 35 U.S.C. 154(b) by 0 days.

(21) Appl. No.: 08/215,395

(22) Filed: Mar. 21, 1994

Related U.S. Application Data

(63) Continuation of application No. 07/776,772, filed on Oct. 15, 1991, now abandoned.

(51) Int. Cl.[7] .............................. A61K 39/42; C07K 16/10
(52) U.S. Cl. .................................... 424/142.1; 424/148.1; 424/160.1; 530/388.15; 530/388.35
(58) Field of Search ............................. 424/142.1, 148.1, 424/160.1, 183.1; 435/70.21, 172.2, 240.27, 451, 452; 530/388.1, 388.15, 388.35, 389.4, 391.7

(56) References Cited

U.S. PATENT DOCUMENTS

| | | | |
|---|---|---|---|
| 5,166,050 | * 11/1992 | Shriver et al. | ............................. 435/5 |
| 5,245,015 | * 9/1993 | Fung et al. | ......................... 530/388.35 |
| 5,922,325 | * 7/1999 | Tilley et al. | ........................ 424/208.1 |

OTHER PUBLICATIONS

Sugita et al., "Use of a Cocktail of Monclonal Antibodies and Human Complement in Selective Killing of Acute Lymphocytic Leukemia Cells", International Journal of Cancer, vol. 37, 1986, pp. 351–357.

Matthews et al., "Restricted Neutralization of Divergent Human T–Lymphotropic Virus Type III Isolates by Antibodies to the Major Envelope Glycoprotein", Proceedings of the National Academy of Sciences, USA, vol. 83 1986, pp. 9709–9713.

McDougal et al., "Binding of HTLV–III/LAV to T4 + T Cells by a Complex of the 110k Viral Protein and the T4 Molecule", Science, vol. 231, Jan. 24, 1986, pp. 382–385.

Sun et al., "Generation and Characterization of Monoclonal Antibodies to the Putative CD4–Binding Domain of Human Immunodeficiency to the Putative CD4–Binding Domain of Human Immunodeficiency Virus Type 1 gp120", Journal of Virology, vol. 63, No. 9, Sep. 1989, pp. 3579–3585.

Skinner et al., "Neutralizing Antibodies to an Immunodominant Envelope Sequence Do No Prevent gp120 Binding to CD4", Journal of Virology, vol. 62, No. 11, Nov. 1988, pp. 4195–4200.

Ho et al., Abstract, "A Neutralizing Human Monoclonal Antibody (HMab) Identifies an Epitope Within the Putative CD4–Binding Domain (CD4–BD) of HIV–1 gp120", *Volume 1 Abstracts*, Th.A.76, 1990.

Berman et al., "Protection of chimpanzees from infection by HIV–1 after vaccination with recombinant glycoprotein gp120 but not gp160", *Nature*, 345: 622–625, 1990.

Devash et al., "Vertical transmission of human immunodeficiency virus is correlated with the absence of high–affinity/avidity meternal antibodies to the gp120 principal neutralizing domain", *PNAS*, 87: 3445–3449, 1990.

Girard et al., "Immunization of chimpanzees confers protection against challenge with human immunodeficiency virus", *PNAS*, 88: 542–546, 1991.

Gorny et al., "Generation of human monoclonal antibodies to human immunodeficiency virus", *PNAS*, 86: 1624–1628, 1989.

Ho et al., "Conformational Epitope on gp120 Important in CD4 Binding and Human Immunodeficiency Virus Type 1 Neutralization Identified by a Human Monoclonal Antibody", *J. Virol.*, pp. 489–493.

Lasky et al., "Delineation of a Region of the Human Immunodeficiency Virus Type 1 gp120 Glycoprotein Critical for Interaction with the CD4 Receptor", *Cell*, 50: 975–985, 1987.

Olshevsky et al., "Identification of Individual Human Immunodeficiency Virus Type 1 gp120 Amino Acids Important for CD4 Receptor Binding", *Journal of Virology*, 64(12): 5701–5707, 1990.

Robinson et al., "Human monoclonal antibodies to the human immunodeficiency virus type 1 (HIV–1) transmembrane glycoprotein gp41 enhance HIV–1 infection in vitro", *PNAS*, 87: 3185–3189, 1990.

Robinson et al., "Identification of Cnserved and Variant Epitopes of Human Immunodeficiency Virus Type 1 (HIV–1) ap120 by Human Monoclonal Antibodies Produced by EBV–Transformed Cell Lines", *Aids Research and Human Retroviruses*, 6(5); 567–579, 1990.

Till et al., "Human immunodeficiency virus–infected T cells and monocytes are killed by monoclonal human anti–gp41 antibodies coupled to ricin A chain", *PNAS*, 86: 1987–1991, 1989.

(List continued on next page.)

Primary Examiner—Robert D. Budens
(74) Attorney, Agent, or Firm—Browdy and Neimark

(57) ABSTRACT

Human monoclonal antibodies specific for the CD4-binding domain of HIV gp120 are useful in the neutralization of HIV and in the prevention of HIV infection and the treatment of a subject infected with HIV. Such antibodies and heterohybridomas producing them are disclosed. Synergistic mixtures of at least two human monoclonal antibodies specific for two different epitopes of gp120 are used to neutralize HIV, to prevent HIV infection and to treat a subject infected with HIV. In this synergistic mixture, one antibody has broad HIV group specificity, and is preferably specific for the CD4-binding domain. The other antibody is preferably specific for the V3 loop and has a range of neutralizing activity such that it neutralizes virus of the MN strain, MN-like families, and widely divergent HIV-1 isolates which are members of various V3 lop classes.

42 Claims, 8 Drawing Sheets

OTHER PUBLICATIONS

Tilley et al., "A human monoclonal antibody against the CD4–binding site of H1V1 gp120 exhibits potent, broadly neutralizing activity", *Res. Virol.*, 142: 247–259, 1991.

Fahey et al., "Status of Immune–Based Therapies in HIV Infection and AIDS," *Clin. Exp. Immunol.* 88:1–5, 1992.*

Zolla–Pazner et al., "Passive Immunization for the Prevention and Treatment of HIV Infections," *AIDS* 6:1235–1247, 1992.*

Rhame et al., "Phase I Trial of HIV Immune Globulin In Persons With AIDS," *Intl. Conf. on AIDS* 3:211 (Abstract No. S.B.500), 1990.*

Perrillo et al., "Immune Globulin and Hepatitis B Immune Globulin," *Arch. Intern. Med.* 144:81–85, Jan. 1984.*

Prince et al., "Apparent Prevention of HIV Infection by HIV Immunoglobulin Given Prior to Low–Dose HIV Challenge," *Vaccines 90*, pp. 347–351, 1990.*

Emini et al., "Antibody–Mediated In Vitro Neutralization of Human Immunodeficiency Virus Type 1 Abolishes Infectivity for Chimpanzees," *J. Virol* 64(8):3674–3678, Aug. 1980.*

Jackson et al., "Passive Immunoneutralization of Human Immunodeficiency Virus In Patients With Advanced AIDS," *The Lancet*, Sep. 17, 1988, pp. 647–652.*

Thali et al., "Discontinuous, Conserved Neutralization Epitopes Overlapping the CD4–Binding Region of Human Immunodeficiency Virus Type 1 gp120 Envelope Glycoprotein," *J. Virol* 66(9):5635–5641, Sep. 1992.*

McKeating et al., "Amino Acid Residues of the Human Immunodeficiency Virus Type 1 gp120 Critical for the Binding of Rat and Human Neutralizing Antibodies That Block the gp120–sCD4 Interaction," *Virology* 190:134–142, 1992.*

Robinson et al., "Identification of Conserved And Variant Epitopes of Human Immunodeficiency Virus Type 1 (HIV–1) gp120 by Human Monoclonal Antibodies Produced by EBV–Transformed Cell Lines," *AIDS Res. Human Retroviruses* 6(5):567–577, May 1990.*

Tilley et al., "Potent Neutralization of HIV–1 by Human and Chimpanzee Monoclonal Antibodies Directed Against Three Distinct Epitopes Clusters of gp120," *Sixieme Colloque Des Cent Garates*, p 211–216, 199.*

Tilley et al., "Human Monoclonal Antibodies Against The Putative CD4 Binding Site And The V3 Loop of HIV gp120 Act In Concert To Neutralize Virus," *VII Intl. Conf. on AIDS*, Florence, Italy, Abstract No. M.A.70, Jun. 17, 1991.*

Fox, J.L., "No Winners Against AIDS," *Bio/Technology* 12:128, Feb. 1994.*

* cited by examiner

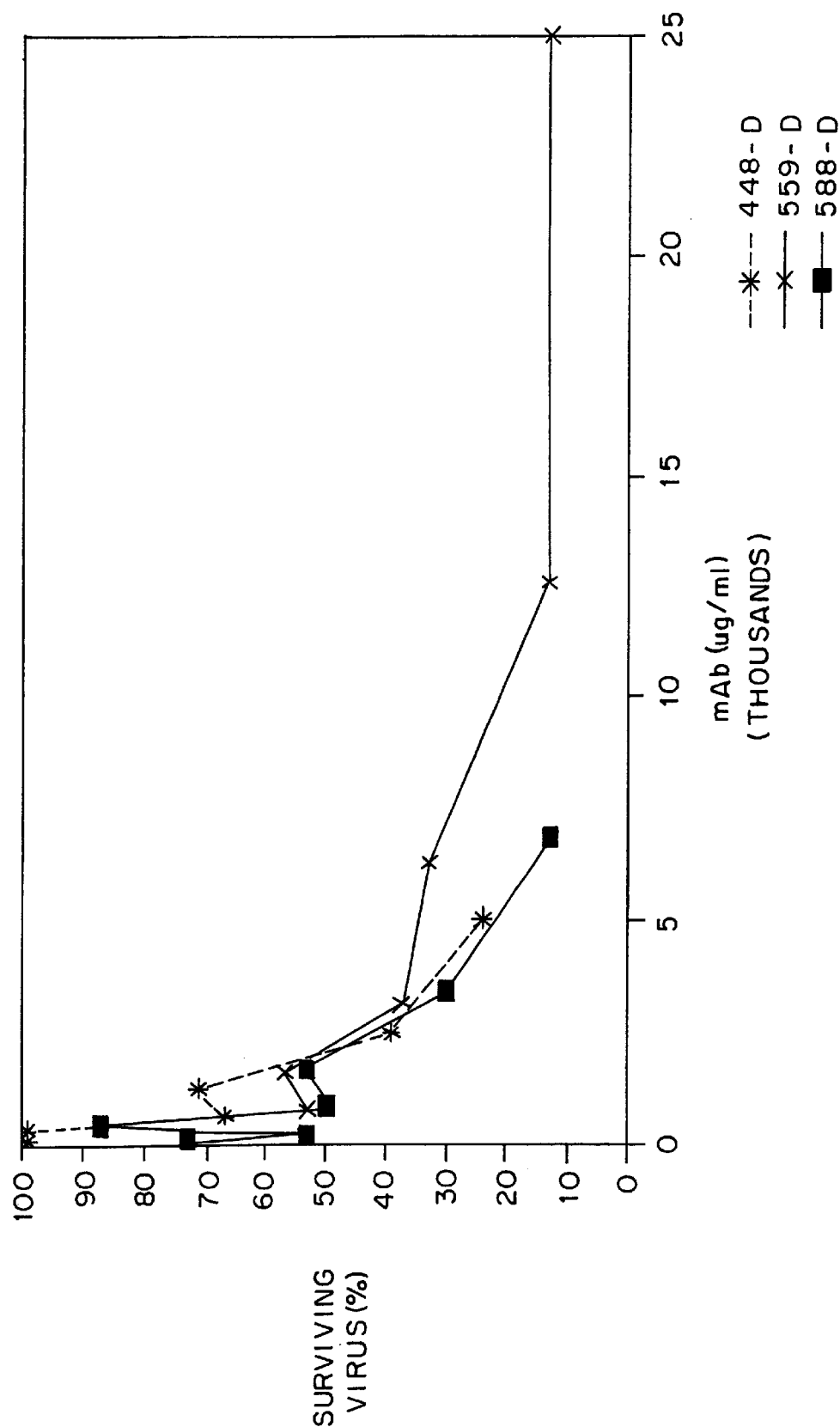

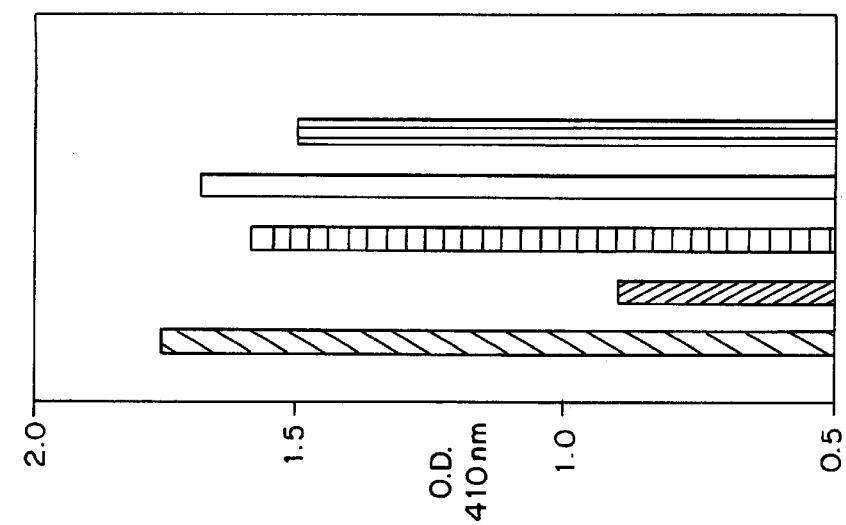
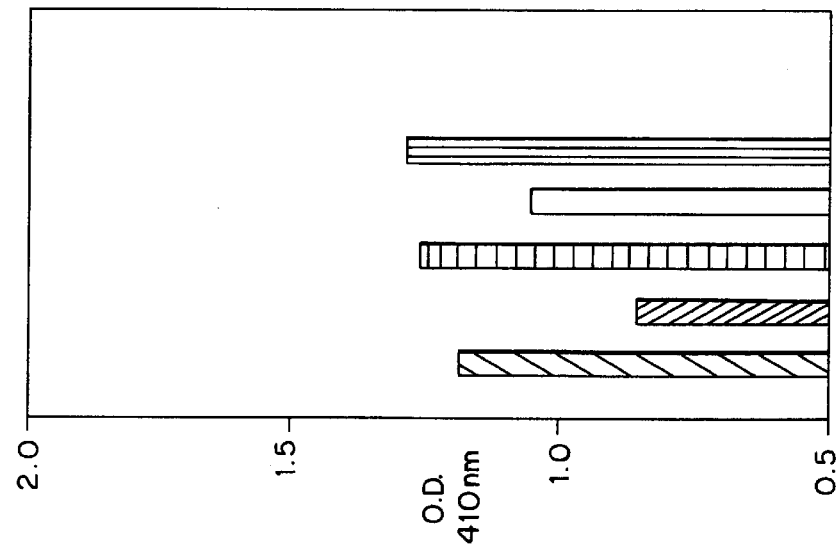
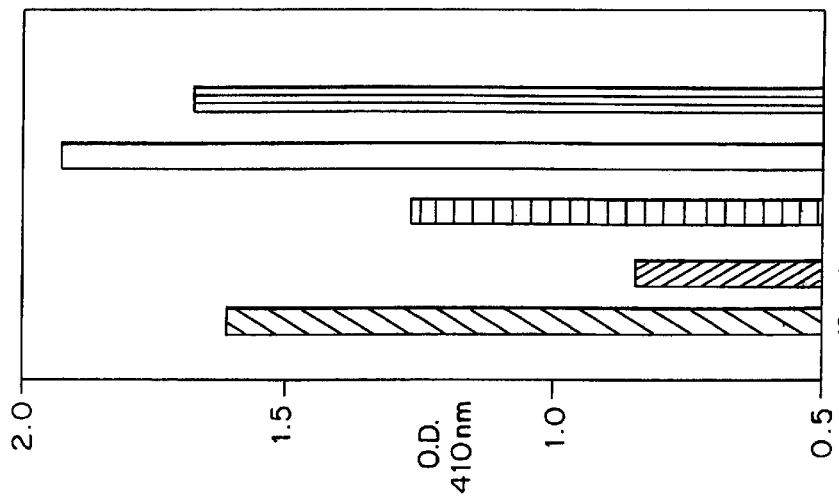

HUMAN MONOCLONAL ANTIBODIES TO THE CD4-BINDING DOMAIN OF HIV, USES THEREOF AND SYNERGISTIC NEUTRALIZATION OF HIV

CROSS-REFERENCE TO RELATED APPLICATION

This application is a continuation of application Ser. No. 07/776,772, filed Oct. 15, 1991, now abandoned.

This invention was funded in part by a research contract from the National Institute of Allergy and Infectious Disease, National Institutes of Health, No. AI 27742 and AI72658, which provides to the United States Government certain rights in this invention.

BACKGROUND OF THE INVENTION

1. Field of the Invention

The present invention in the fields of immunology and virology relates human monoclonal antibodies specific for the CD4-binding domain of HIV gp120 and their uses in neutralizing HIV and in treating HIV infection. Also provided is a composition comprising a mixture of at least two antibodies specific to different HIV gp120 epitopes, preferably in the V3 domain and the CD4-binding domain, which synergize in the neutralization of HIV.

2. Description of the Background Art

The human immunodeficiency virus (HIV) has been implicated as the causative agent of acquired immune deficiency syndrome (AIDS). Two different HIV families have been identified to date: HIV-1 and HIV-2. It is currently believed that the majority of individuals that become infected with HIV eventually will develop AIDS and are likely to succumb to fatal infections and/or malignancies. Currently, it is estimated that approximately 1.5 million persons have been infected by HIV in the United States alone. Thus, treatment and prevention of HIV infection is among the leading public health challenges today.

Chemotherapy of patients afflicted with AIDS or HIV infections with antiviral drugs, such as azidothymidine (AZT), has led to some clinical and immunological improvement and has decreased the mortality rate and frequency of opportunistic infections. However, such drugs are expensive, may induce resistant strains of HIV, and have numerous toxic side effects, and may therefore not be suitable for administration to all AIDS patients.

Immunotherapeutic approaches to AIDS include use of monoclonal antibodies (mAbs) of defined specificity directed against HIV-1 proteins expressed in infected patients. These HIV-1 virion proteins, expressed by infected cells, are designated inter alia as p24, gp41, gp120, etc. (See, for example, Essex, U.S. Pat. No. 4,725,6569.

Passive immunization has been used to prevent and treat many bacterial and viral illnesses (Zolla-Pazner S. et al., *J. Virol. Meth.* 17:45–53 (1987)) and has been shown to prevent the infection of chimpanzees with HIV-1 (Emini E. A. et al., *J. Virol.* 64:3674–3678 (1990); Prince A. M. et al., In: *Vaccines 90: Modern Approaches to New Vaccines Including Prevention of AIDS*, Brown, F., ed, Cold Spring Harbor Laboratories Press, Cold Spring Harbor, N.Y., 1990, pp. 347–351). Given these precedents, it is likely that passive immunotherapy may be useful in (a) preventing HIV infection in health care workers after accidental exposure, (b) blocking transmission of HIV from the infected mother to her fetus and (c) treating previously HIV-infected patients. It is generally thought that useful antibodies for the treatment of HIV infection are those capable of neutralizing HIV, by either simple binding to a virion component or by antibody-mediated inhibition of viral functions such as binding to the cell surface receptor, the CD4 molecule. Furthermore, it is generally accepted that human mAbs to HIV would be preferable because of their lack of foreign antigenic sites that may lead to a host immune response against the antibody. An optimal passive immunotherapeutic agent would comprise a human antibody preparation which could be administered intramuscularly and which would neutralize a majority, if not all, HIV-1 strains.

A number of human monoclonal antibodies (mAbs) to HIV have been produced. Several of the human mAbs specific for gp120 possess neutralizing activity (Gorny M. K. et al., *Proc. Natl. Acad. Sci. (USA)* 88:3238–3242 (1991); Robinson J. E. et al., *AIDS Res. Hum. Retrovir.* 6:567–579 (1990); Posner M. R. et al., *J. Immunol.* 146:4325–4331 (1991); Ho D. D. et al., *J. Virol.* 65:489–493 (1991); Tilley, S. A. et al., *Research Virol.* 142:247–259 (1991)). These mAbs have generally been categorized as "type-specific" or "group-specific". Type-specific mAbs are generally directed against the V3 loop of gp120 (Goudsmit J. et al., *FASEB J.* 5:2427–2436 (1991); Nara P. L. et al., *FASEB J.* 5:2437–2455 (1991)) and by definition are restricted in their biologic function to one or a few related HIV-1 isolates. Some group-specific mabs are directed against a large conformational region of gp120 responsible for binding to CD4 (Goudsmit et al., supra; Nara et al., supra); these mAbs generally neutralize many (but not all) HIV-1 isolates.

Some of the neutralizing epitopes of HIV are located in conserved regions of the proteins (Ho, D. D. et al., *Science* 239: 1021 (1988)). However, they do not seem to elicit particularly strong immune responses nor to serve as appropriate neutralizing domains since (a) serum titers of antibodies recognizing these epitopes are generally low, and (b) high concentrations of murine mAbs to these epitopes are required to achieve neutralization.

Several studies have reported that the principal neutralizing epitope of HIV-1 appears to reside in the V3 domain of gp120 (Goudsmit, J. et al., *Proc. Natl. Acad. Sci. USA* 85:4478–4482 (1988); Goudsmit, J. *AIDS* 2:S41 (1988); Matsushita, S. M. et al.,*J. Virol.* 62:2107 (1988); Javaherian, K. et al., *Proc. Natl. Acad. Sci. USA* 86:6768 (1989); Kowalski et al.,*Science* 237:1351 (1987); Palker et al.,*Proc. Natl. Acad. Sci. USA* 85:1758–1762 (1988)). The V3 loop has a "tip" which consists of an essentially conserved sequence of four amino acids, Gly-Pro-Gly-Arg (G-P-G-R; SEQ ID NO:1) flanked by amino acid residues which vary among HIV-1 isolates. The V3 loop has been shown to be important for infectivity (Stephens et al., *Nature* 343:219 (1990); Hattori et al., *FEBS Lett.* 248:48 (1989)).

The interaction of the gp120 external envelope glycoprotein with CD4 is the principal step leading to the entry of HIV-1 into CD4+ cells (Dalgleish, A. G. et al., *Nature* 312:763–767 (1984)). The structure of the CD4-binding domain of gp120 is not yet fully elucidated. Substitution of individual amino acids, deletion of several residues, or truncation of large C-terminal fragments altered CD4-gp120 binding (Cordonnier, A. et al., *Nature* 340:571–574 (1989); Kowalski, M. et al., *Science* 237:1351–1355 (1987); Ardman, B. et al., *J. AIDS* 3:206–214 (1990)). Olshevsky et al. (*J. Virol.* 64:5701–5707 (1990)) recently demonstrated that structure of the CD4-binding domain included contributions from the second, third, and fourth conserved regions of gp120, thus indicating that it is a conformational epitope.

In natural infections, the immune responses to the V3 loop and the CD4-binding domain are quite different. While antibodies to the V3 loop develop early in the course of HIV infection, their titer appears to wane during the first year or two (Blattner, W. et al., *Int'l. Conf. AIDS* 5:510 (1989)). In contrast, antibodies to the CD4-binding domain arise more slowly but appear to persist for longer periods (Ho D. D. et al., *J. Virol.* 65:489–493 (1991)). Since a CD4-binding domain is common to all competent HIV-1 viruses, antibodies to this region, which are generally neutralizing, would be expected to offer a relatively broad range of protection. Thus, in order to (a) better characterize the human immune response to HIV, (b) formulate vaccines that can induce broadly protective antibodies and (c) use such antibodies in passive immunotherapy, it is important to understand the specificity of these antibodies and the mechanism by which they protect against disease.

Monoclonal antibodies (mAbs) to the CD4-binding domain of gp120 have previously been disclosed. Some of these inhibit CD4-gp120 binding but do not neutralize virus infectivity (Sun, H. et al., *J. Virol.* 63:3579–3585 (1989)). Other mAbs, both murine (Sun, H. et al., supra) and human (Robinson J. E. et al., supra; Posner M. R. et al., supra; Tilley, S. A. et al., supra), inhibit CD4-gp120 binding and also neutralize HIV infectivity. At least three neutralizing mAbs (two murine and one human) specific for the CD4-binding domain do not cross-compete (Ho, D. D. et al., *J. Virol.* 65:489–493 (1991)). These findings, in combination with the current structural understanding of the CD4-binding domain, provide further support for the conclusion that the CD4-binding domain exists as a large, conformation-dependent, discontinuous epitope on the surface of the gp120 molecule.

Thus, for purposes of both research and therapy, there is a recognized need in the art for human mAbs with broad virus group specificity to the CD4-binding domain. In particular, it would be advantageous to obtain such mAbs using a variety of screening techniques to insure the diversity of the mAbs selected. The production of new human mAbs specific for the CD4-binding domain of gp120 thus constitute one objective of the present invention (see below).

Finally, synergy between antibodies has been demonstrated in the neutralization of a number of viruses (Della-Porta A. J. et al., *J. Gen. Virol.* 38:1–19 (1977); Henchal E. A. et al. *J. Gen. Virol.* 69:2101–2107 (1988); Wensvoort G., *J. Gen. Virol.* 70:2865–2876 (1989)). Studies from the present inventors' laboratory showed that different human mAbs specific for the HIV glycoprotein gp41 acted synergistically. However the effect of this synergy was not better neutralization but rather antibody-dependent enhancement of HIV infection (Robinson, W. E. Jr. et al., *Proc. Natl. Acad. Sci. (USA)* 87:3185–3189 (1990); Robinson W. E. Jr et al., *J. Virol.* 65:4169–4176 (1991)).

Tilley et al. (Proc. 7th Int'l. Conf. on AIDS, Florence, Italy (Jun. 16–21, 1991), abstr. M.A.70) disclosed that a V3 specific human mAb, 4117C, acted in concert with a CD4-binding domain-specific human mAb, 1125H, in neutralizing HIV. Importantly, however, the V3 antibody had a limited range of reactivity, reacting with V3 of MN, SF-2 and NY-5 isolates of HIV but not with RF or IIIB strains. Furthermore, this reference did not determine whether the two antibodies were synergistic.

It is therefore important to identify synergistic interactions between other, more broadly reactive, anti-HIV antibodies that result in both improved virus neutralization and a broader range of reactivity, which can be exploited in AIDS immunotherapy.

SUMMARY OF THE INVENTION

It is an object of the present invention to overcome the aforementioned deficiencies in the work described above.

The present inventors have produced and analyzed several novel human mAbs reactive with the CD4-binding domain of gp120. The present inventors used gp120 from one particular strain of HIV-1, HTLV-IIIB, as a screening antigen, and started with cells from naturally infected patients as their approach to assure the selection of mAbs with broad group reactivity. The discoveries detailed herein demonstrate that the CD4-binding domain is immunogenic, as three of the four mAbs of the present invention described herein, were reactive with this region. Furthermore, the results suggest that most, if not all antibodies to the CD4-binding domain in naturally infected hosts are neutralizing antibodies, since three mAbs specific for this region had potent virus neutralizing activity.

In addition, the present inventors have discovered that appropriate combinations of antibodies specific for two different gp120 epitopes, the CD4-binding domain and the V3 loop, interact synergistically to result in greater than expected virus neutralization and enhanced host range of specificity.

The present invention is directed to an antibody specific for an epitope of the CD4-binding domain of gp120, the antibody being a human monoclonal antibody which is group-specific, neutralizing, and capable of binding to gp120 when the gp120 is bound to an immobilized anti-V3 loop antibody.

The present invention is also directed to a human monoclonal antibody specific for an epitope of the CD4-binding domain of gp120, wherein the antibody is selected from the group consisting of human monoclonal antibody 448-D, 559/64-D, 588-D and an antibody which blocks the binding of human monoclonal antibody 448-D, 559/64-D or 588-D to gp120.

In one embodiment, the antibody is the human monoclonal antibody 448-D or an antibody which blocks the binding of human monoclonal antibody 448-D to gp120. In another embodiment, the antibody is the human monoclonal antibody 559/64-D or an antibody which blocks the binding of human monoclonal antibody 559/64-D to gp120. In yet another embodiment, the antibody is the human monoclonal antibody 588-D or an antibody which blocks the binding of human monoclonal antibody 588-D to gp120.

The present invention is further directed to a cell line producing any of the above human monoclonal antibodies. Preferably, the cell line is a human-mouse heterohybridoma. Preferred cell lines are 448-D (ATCC #HB 10895), 559/64-D (ATCC #HB 10893) or 588-D (ATCC #HB 10894).

The present invention also includes a method for neutralizing HIV comprising contacting the HIV with an effective amount of the above antibody.

Also provided is a method for preventing infection by HIV in a subject or treating a subject infected with HIV, comprising administering to the subject an effective amount of the above antibody.

The present invention is also directed to a composition useful for neutralizing HIV, for preventing infection by HIV-1, or for treating a subject infected with HIV, comprising an effective amount of a mixture of at least a first and a second antibody specific for different epitopes of the HIV gp120 protein, wherein (a) the first antibody is group-specific; and (b) the second antibody is specific for the V3 region of gp120, and has a range of neutralizing activity such that it neutralizes MN, MN-like families, and widely divergent HIV-1 isolates which are members of various V3 loop classes, including RF and IIIB, and wherein the neutralizing activity of the mixture is greater than the sum of the neutralizing activity of each antibody alone. In a preferred embodiment, the second antibody neutralizes both the MN and RF strains or both the MN and IIIB strains of HIV-1.

Preferably, in the above composition, the first and the second antibody are monoclonal antibodies, more preferably, human monoclonal antibodies. A preferred first antibody is specific for the CD4-binding domain of gp120, and a preferred second antibody is specific for the V3 domain of gp120. Preferably, the first antibody of this composition is a human monoclonal antibody which is group-specific, neutralizing, and capable of binding to gp120 when the gp120 is bound to an immobilized anti-V3 loop antibody. More preferably, (1) the first antibody is selected from the group consisting of 448-D, 559/64-D, 588-D and an antibody which blocks the binding of 448-D, 559/64-D or 588-D to gp120, and (2) the second antibody is the human monoclonal antibody 447-52D (referred to below also as 447-D).

Also provided is a method for neutralizing HIV comprising providing to the HIV the composition described above, thereby neutralizing the virus.

In another embodiment, the invention provides a method for preventing HIV infection in a subject or treating a subject infected with HIV, comprising administering to the subject an effective amount of the composition described above, thereby preventing the infection or treating the subject.

The present invention is directed to a pharmaceutical composition comprising an antibody specific for an epitope of the CD4-binding domain of the gp120, the antibody being a human monoclonal antibody which is group-specific, neutralizing, and capable of binding to gp120 when the gp120 is bound to an immobilized anti-V3 loop antibody, and a pharmaceutically acceptable excipient. Preferably, in this pharmaceutical composition, the antibody is selected from the group consisting of human monoclonal antibody 448-D, 559/64-D, 588-D and an antibody which blocks the binding of human monoclonal antibody 448-D, 559/64-D or 588-D to gp120.

Another pharmaceutical composition of the present invention comprises the composition described above having at least a first and a second antibody, and a pharmaceutically acceptable excipient.

BRIEF DESCRIPTION OF THE DRAWINGS

FIG. 7 is a graph showing neutralization of $HIV-1_{MN}$ by various human mAbs.

FIG. 8 is a graph showing the results of immunochemical blocking experiments in ELISA. The ordinate is absorption at 410 nm. The antibodies of the present invention specific for the CD4-binding domain are shown to be distinct from other known antibodies specific for the same region.

DESCRIPTION OF THE PREFERRED EMBODIMENTS

Figure 1:
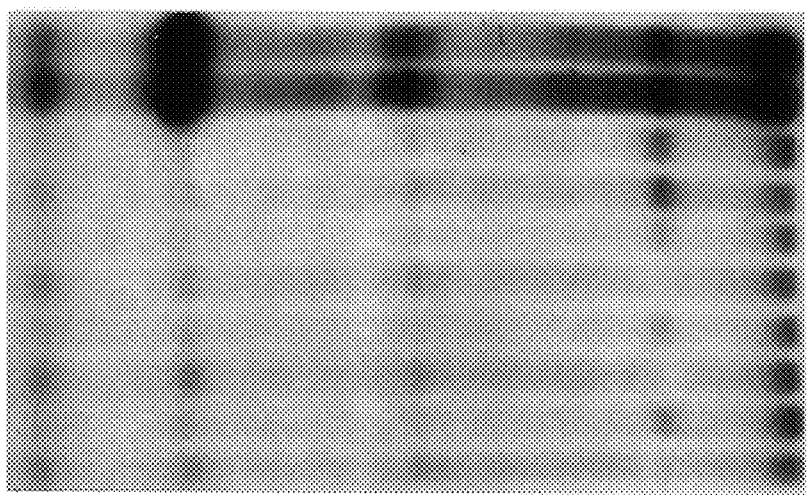
FIG. 1 is a group of gel patterns which show precipitation of HIV proteins by several human mAbs in a radioimmunoprecipitation assay.
Figure 2:
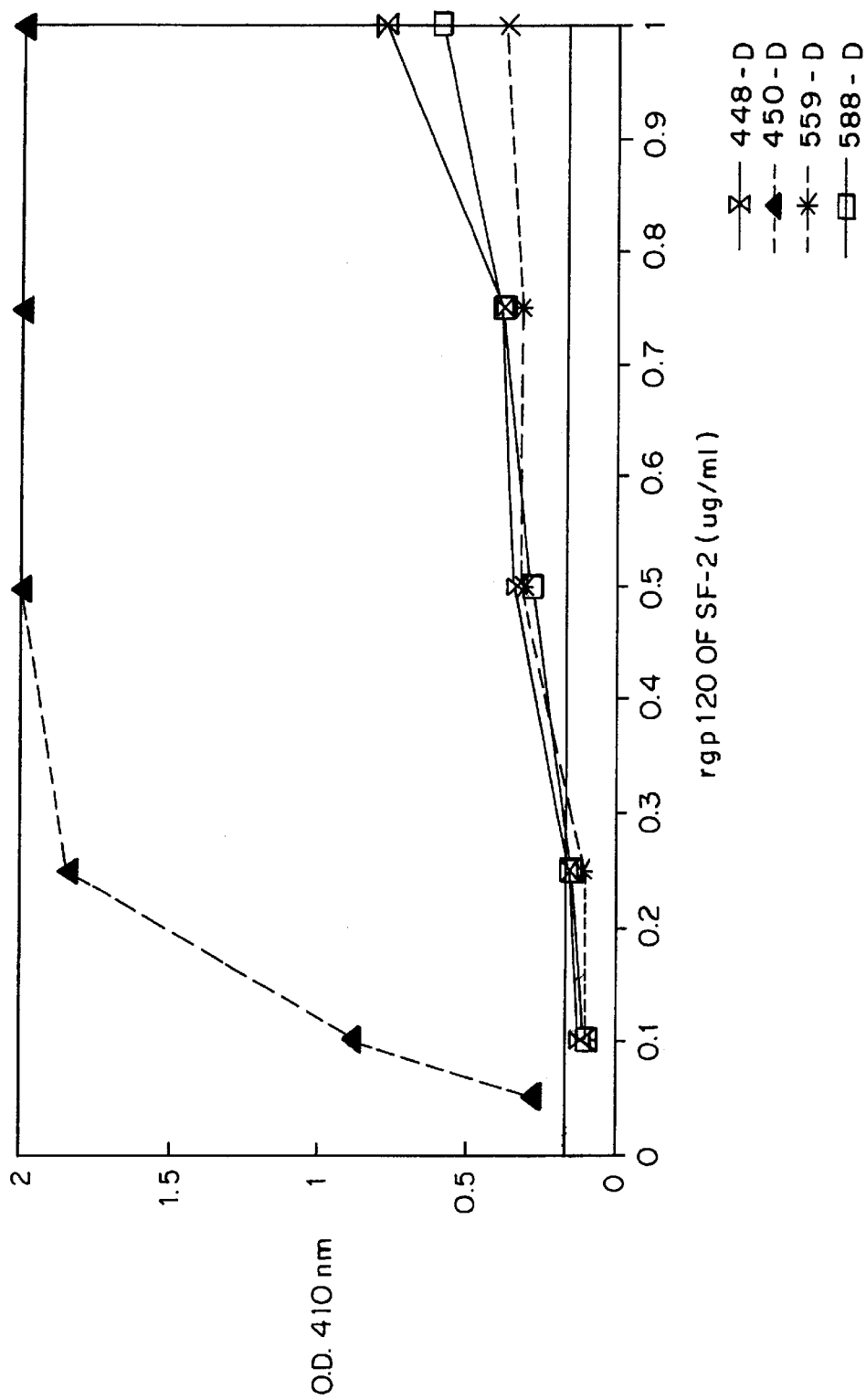
FIG. 2 is a graph showing binding of various human mAbs with $gp120_{SF-2}$ bound directly to an ELISA plate.
Figure 3:
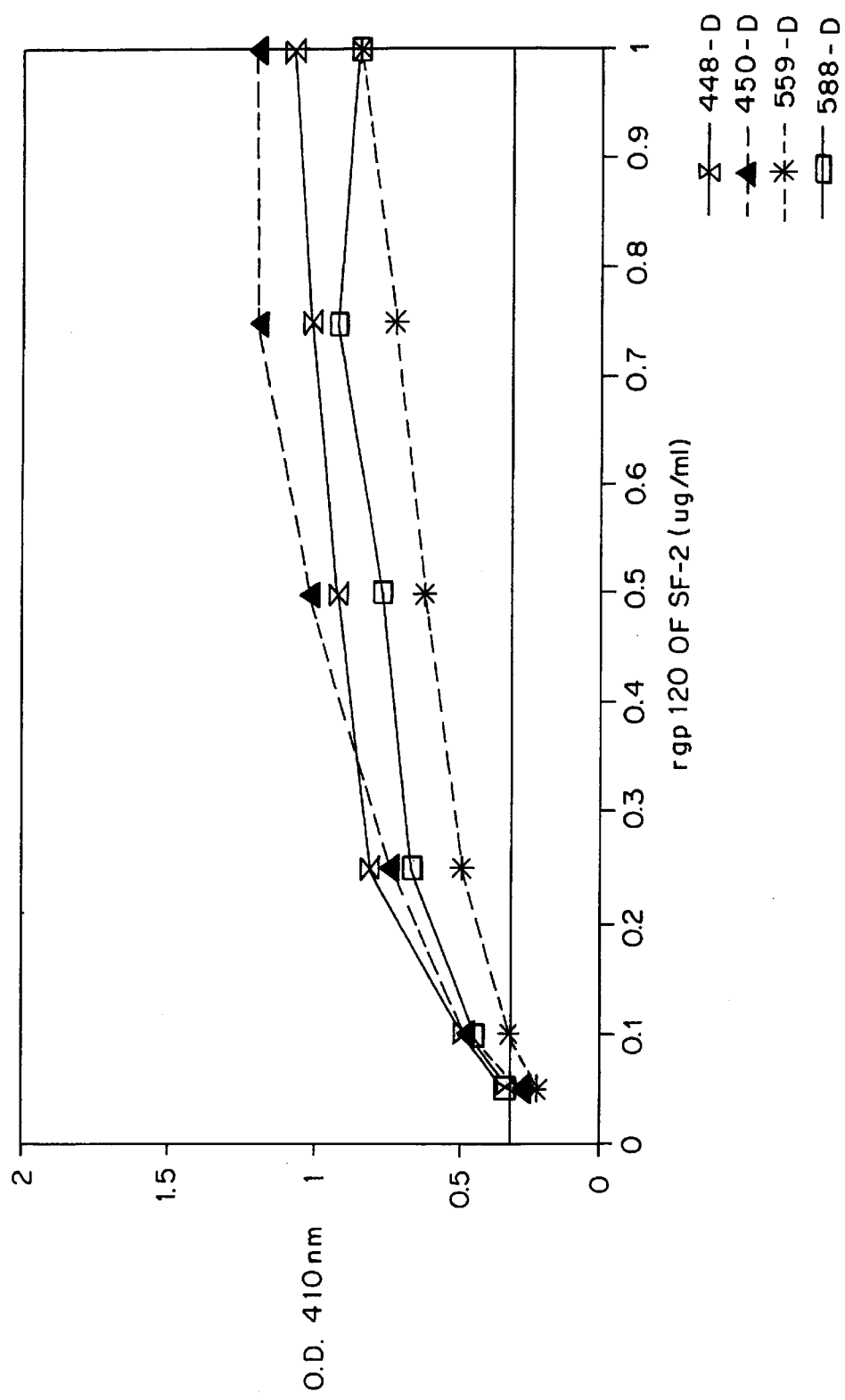
FIG. 3 is a graph showing binding of various human mAbs with $gp120_{SF-2}$ bound indirectly to an ELISA plate via Concanavalin A.
Figure 4:
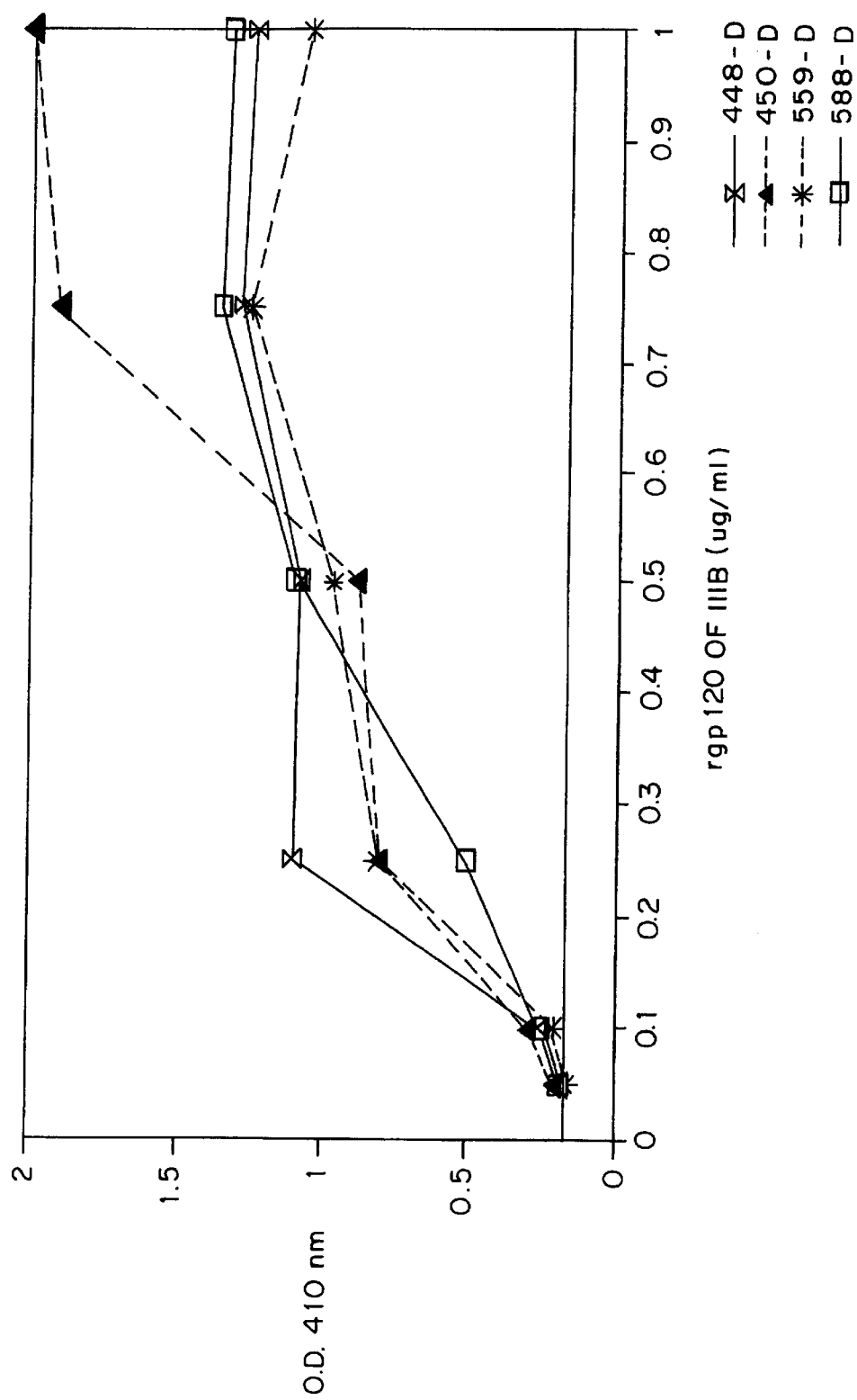
FIG. 4 is a graph showing binding of various human mAbs with $gp120_{III-B}$ bound directly to an ELISA plate.
Figure 5:
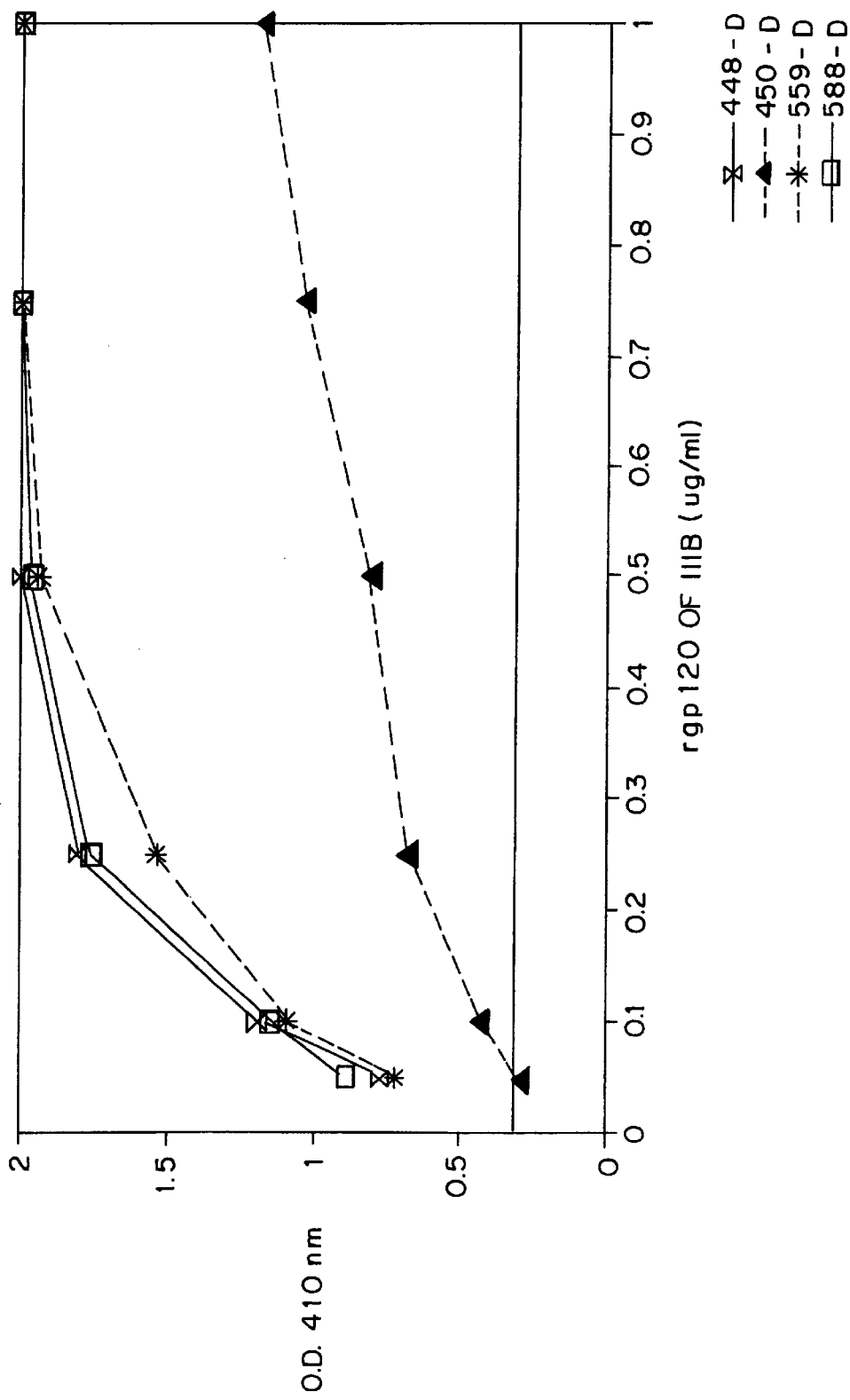
FIG. 5 is a graph showing binding of various human mAbs with $gp120_{III-B}$ bound indirectly to an ELISA plate via Concanavalin A.

The present invention is directed first to novel human monoclonal antibodies (mAbs) specific for the CD4-binding domain of the HIV glycoprotein, gp120, which have the capacity to neutralize viral infectivity. The invention is further directed to use of a combination of these antibodies and antibodies specific for a different epitope of gp120, in the V3 loop, to neutralize HIV and prevent or treat HIV infection in a synergistic manner.

Cell lines making human IgG mAb to a neutralizing epitope of HIV-1, including epitopes of the V3 loop or the CD4-binding domain of the gp120 glycoprotein, are produced by transformation of human peripheral blood mononuclear cells with Epstein-Barr virus (EBV), selection of cell lines making antibody of the desired specificity, followed by fusion of the selected EBV-transformed cells to a heteromyeloma cell line. The resultant heterohybridoma cells each makes a human mAb having the epitope-specificity of the antibody produced by the selected parent EBV-transformed cell.

The gp120 glycoprotein, which contains one or more neutralizing epitopes recognized by the cells and antibodies of the present invention, may be derived from any of the known HIV-1 strains, including the relatively common MN strain, the SF-2 strain, the HTLV-IIIB, strain or any other strain currently known or unknown.

By the term "heteromyeloma" is intended a hybrid cell produced by fusion of a non-human myeloma cell line and a human myeloma cell line. Typically, a mouse myeloma or plasmacytoma cell is the fusion partner of the human myeloma cell. Such non-human and human myeloma and heteromyeloma cell lines are well-known in the art and are exemplified by cell lines reported in Teng, N. N. et al., *Proc. Natl. Acad. Sci. USA* 80:7308 (1983); Kozbor, D. et al., *Hybridoma* 2:7 (1983); and Grunow, R. et al., *J. Immunol. Meth.* 106:257–265 (1988).

As intended in the present invention, heteromyeloma cells are used as fusion partners for selected EBV-transformed human cells to produce the heterohybridomas secreting the human mAbs of this invention. In a preferred embodimnent, the heteromyeloma SHM-D33 is used as a fusion partner. This cell line is available from the ATCC, under accession number ATCC CRL1668.

The term "heterohybridoma", as used herein, refers to a hybrid cell line produced by fusion of an antibody-producing cell of one species with a heteromyeloma. The term "heterohybridoma" has also been used elsewhere to refer to any interspecies hybridoma, such as one resulting from the fusion of a cell of an antibody-producing human lymphocytoid cell line and a murine myeloma cell. However, the term as used herein is more narrowly defined.

By the term "neutralizing epitope" is intended an epitope which, when bound by an antibody specific for this epitope, results in neutralization of the virus. "Neutralization" is intended to encompass any biological activity of the virus. Thus, for example, inhibition of cell-free viral infectivity or of viral syncytium formation falls within the scope of the term "neutralization", as used herein.

To generate human mAbs against a neutralizing epitope of HIV-1 gp120, human peripheral blood lymphocytes are transformed by EBV, as described, for example in Gorny, M. K. et al., *Proc. Nat'l. Acad. Sci. USA* 86:1624–1628 (1989), which is hereby incorporated by reference. Preferably, the cells to be transformed are derived from the blood of an individual producing anti-HIV-1 antibodies.

Screening for an antibody against a particular neutralizing epitope of gp120 is performed using purified gp120, recombinant gp120, a fragment thereof, or a synthetic peptide representing a portion thereof. In one embodiment, cultures are screened for antibody to an epitope of the V3 loop of gp120 using a synthetic 23-mer peptide from the V3 loop representing amino acids 306–328. The numbering system of the MN strain of virus is that of Myers (Myers, *Theoretical Biology and Biophysics*, 1990). In the case of the V3 loop, other peptides having at least 6 amino acids are useful for screening the antibody-secreting cells to identify cells producing antibody of the desired epitope specificity.

Methods for cloning cells, and for screening and assaying supernatants are disclosed in co-pending application Ser. No. 07/684,090, filed Apr. 12, 1991, which is hereby incorporated by reference in its entirety.

Any of a number of immunoassays well known in the art can be used for this screening process. Preferred immunoassays are Enzyme Linked Immunosorbent Assays (ELISA) or radioimmunoprecipitation (RIP) assays. Using such an assay, culture supernatants are tested for the presence of antibodies of desired specificity and isotype. The antigen preparation may comprise HIV-1 virions, lysates of viruses or of infected cells, biochemically isolated or recombinant viral proteins, or recombinant or synthetic viral peptides.

The mAbs of the present invention are preferably of the IgG isotypes and may be recovered from the supernatants of the heterohybridoma cell cultures and purified by conventional methods known in the art for purification of IgG. Such methods include, but are not limited to, protein-A Sepharose affinity chromatography, a combination of Affigel Blue (BioRad, Richmond, Calif.) and Protein-A Sepharose chromatography, or High Performance Liquid Chromatography.

The human mAbs of the present invention may be used in diagnosis, prophylaxis, therapy and in the analysis of HIV proteins on viruses and infected cells.

In particular, the antibodies and methods of the present invention are useful for preventing or treating AIDS. Thus, when administered to humans infected with HIV-1, or at risk for HIV infections, the antibodies of the present invention can provide therapeutic or prophylactic benefits. In particular, the immunotherapeutic method of the present invention is useful for treatment of acutely infected individuals, or those at high risk for acute infection, for example, health care workers who have been exposed via a needle stick to a source of HIV. The methods of the present invention are also useful for blocking transmission of HIV from mother to fetus in utero. Thus, the mAbs or compositions of the present invention can be administered to HIV-infected expectant mothers. Being of the IgG isotype, the mAbs can cross the placenta and reach the fetus. This may prevent infection of the fetus or, alternatively, provide effective therapy for an infected fetus. Furthermore, the mAbs or compositions of the present invention may be administered to the newborn suspected of being infected from the mother, whether or not the mother has been similarly treated.

The human mAbs of the present invention specific for the CD4-binding domain of gp120, as well as the synergistic combination of antibodies disclosed herein, are used to prevent infection with HIV and to treat individuals infected by HIV or suffering from AIDS. An effective dose of one or a combination of antibodies are administered parenterally or enterally by any of a number of known routes. For example, administration may be subcutaneous, intravenous, intramuscular, intraperitoneal, topical, transdermal, or intrathecal. Alternatively, or concurrently, administration may be by the oral or rectal route. The antibodies may also be-administered into the amniotic cavity for in utero treatment. The preferred routes are intravenous and intramuscular.

The dosage of antibody administered will be dependent upon the age, health, and weight of the recipient, kind of concurrent treatment, if any, frequency of treatment, and the nature of the effect desired. Effective amounts of the mAbs are from about 0.1 to about 500 mg per day, and preferably from about 3 to about 30 mg per day. Treatment may require infusion or injection of the antibody over a period of days, weeks, months, or even years, as would be readily ascertained by one of skill in the art.

A typical treatment regimen comprises administration of an effective amount of antibody (either alone or in combination with another antibody) administered over a period of about one week and up to a period of several years. Duration of treatment required to achieve a therapeutic result will vary from patient to patient, depending upon the severity and stage of the illness and the individual characteristics of each patient.

The total dose required for each treatment may be administered by multiple doses or in a single dose. The mAb or combination of mAbs may be administered alone or in conjunction with other therapeutics directed to HIV-1 infection, such as nucleoside analogue drugs, or drugs directed to other disease symptoms, for example anti-infective drugs.

The human mAbs of the present invention specific for the CD4-binding domain of gp120 may thus be used alone or in synergistic combination with other antibodies (see below). Importantly, the CD4-binding domain-specific human mAbs of the present invention are distinct from CD4-binding domain antibodies of the prior art, 15e (Robinson J. E. et al., supra) and F105 (Posner M. R. et al., sudra), in that they cross-block or cross-inhibit the binding of the human mAb 448-D, 559/64-D or 588-D (see below for deposit information) to gp120 or an epitope thereof in an immunoassay. Such cross-inhibition is exemplified in FIG. 8. Furthermore, the results shown in Table 2 (below) suggest that an epitope in the CD4-binding domain recognized by the 15e and F105 antibodies is lost upon binding of gp120 to an immobilized anti-V3 antibody, whereas the epitope recognized by the antibodies of the present invention remains. Thus, on the basis of both types of experiments, it may be concluded that the human mAbs disclosed by Robinson et al. and Posner et al. are distinct from those of the present invention and are reactive to a different epitope of the CD4-binding domain. Thus, one of ordinary skill in the art can produce a human mAb according to the present invention using the methods taught herein, and can test, for example, whether the antibody inhibits binding of either 448-D, 559/64-D or 588-D to gp120 using standard immunoassays without undue experimentation.

An important aspect of the present invention is based on the finding that appropriate combinations of anti-HIV mAbs with different epitope specificity provide a broader spectrum of protection than expected on the basis of the neutralization activity of each antibody alone. In one embodiment, the synergistic combination comprises at least a first group-specific antibody specific for a conserved region of gp120 and a second antibody having a range of neutralizing activity such that it neutralizes MN-like families and widely divergent HIV-1 isolates which are members of various V3 loop classes and include, but are not limited to RF and IIIB. As an example, an antibody having such a range would neutralize viruses of both the MN and RF strains or viruses of both the MN and IIIB strains. A preferred example of an antibody having such a range is human mAb 447-D.

By the term "group-specific" is intended an antibody with broad reactivity which is primarily directed to a conserved epitope or region present on a large range, if not all, of HIV-1 viruses. Thus, the antibody of the present invention specific for an epitope of the CD4-binding domain is an example of a group-specific antibody.

In a preferred method and a preferred composition based upon a synergistic combination of neutralizing antibodies, the first antibody is specific for the gp120 CD4-binding domain, and the second antibody is a broadly-specific antibody specific for a conserved epitope of the gp120 V3.

It is believed that the role of the antibody specific for the CD4-binding domain is of particular importance in protecting against infection and in slowing disease progression by virtue of its recognition of a wide array of (if not all) HIV-1 strains. Preferred antibodies specific for the CD4-binding domain for use in the combination above include 448-D, 559/64-D and 588-D (see below for deposit information).

Anti-V3 antibodies known in the art are typically "type-specific" in that react with one or a few related strains of HIV-1, and are commonly specific to linear or sequential determinants of the V3 loop. A preferred anti-V3 loop antibody useful in the compositions and methods of the present invention is one which is not conventionally type-specific, but rather, one that is broadly reactive among more than one unrelated virus strain. A more preferred anti-V3 loop antibody is one which is broadly reactive, having a range of neutralizing activity such that it neutralizes the HIV-1 strain MN, MN-like families of viruses (such as those common in American isolates), and widely divergent HIV-1 isolates which are members of various V3 loop classes, including RF and IIIB strains. A most preferred human mAb of this type is 447-D, produced by several clones of the human-mouse heterohybridoma line, 447-D, such as 447-52D ATCC #HB 10725), preferably the 447-52DIV (ATCC #HB 10891).

This aspect of the present invention draws on the inventors' understanding of the structural basis of the V3 loop structure, the appearance of various amino acid sequences from this region in HIV-1 isolates from different parts of the world, and the reactivity of known mAbs to V3 structures. Accordingly, a preferred broadly reactive V3 loop-specific antibody useful in neutralizing a broad range of American and European HIV-1 isolates is one which recognizes a conformational determinant requiring the presence of the amino acid sequence GPXR (wherein X is any of several amino acid residues), independent of the flanking sequences (corresponding to positions 312–315 of the MN strain; Myers, supra). A similarly broadly reactive antibody useful for neutralizing HIV-1 having the characteristics of the common African isolates is specific for linear epitope including the sequence GPXR (SEQ ID NO:2, GPGX (SEQ ID NO:3) or GLGQ (SEQ ID NO:4), independent of the flanking sequences. Thus, based on the teachings of the present inventors as to methods for obtaining and selecting appropriate antibodies, and the structural requirements in the antibody's specificity, one of ordinary skill in the art will be able to prepare a broadly reactive V3 loop-specific antibody, including such a human mAb, having the desired characteristics pointed out above, without undue experimentation.

The combination of these two types of antibodies, a group-specific antibody specific for the CD4-binding domain of gp120 and a broadly reactive V3 loop-specific antibody, results in a synergistic effect wherein the potency of both individual antibodies is enhanced, and, importantly, at certain concentrations or doses, the effective range of biological activity of the anti-V3 antibody is extended.

According to the present invention, a synergistic combination of antibodies is any in which either: (a) the neutralizing activity of the combination is greater than the expected additive neutralization of either antibody alone; or (b) the virus host range of neutralizing activity is broader than that achieved by the more potent neutralizing antibody alone at that same level of neutralization.

Thus, in light of the present invention, it is apparent that an optimal HIV vaccine should be designed so as to stimulate both anti-V3 and anti-CD4-binding domain antibodies, resulting in the type of synergy described herein and yielding more potent protection against HIV. This concept is further emphasized by the recent findings of K. S. Steimer et al. (*Science* 254:105–109 (1991)) which show that natural anti-HIV-1 antibodies from infected humans neutralize a broader spectrum of HIV isolates than do sera from animals immunized with purified gp120 subunits, due in part to antibodies to conserved gp120 conformational epitopes (including CD4-binding epitopes). In line with the concepts developed by the present inventors, Steimer et al. also suggested that a subunit vaccine presenting such conformational epitopes should lead to broader protection against a range of HIV-1 variants. According to the present invention, optimal passive immunotherapy should utilize a mixture of antibodies that have specificity at least for a variable, semi-conserved or conserved V3 epitope and the CD4-binding domain.

Pharmaceutical compositions comprising the antibodies of the invention include all compositions wherein the antibody or combination of antibodies is contained in an amount effective to achieve its intended purpose. In addition to the antibody, the pharmaceutical compositions may contain suitable pharmaceutically acceptable carriers comprising excipients and auxiliaries which facilitate processing of the active compounds into preparations which can be used pharmaceutically. An additional pharmaceutical composition within the scope of the present invention is a combination of the antibody of the invention with an intravenous immunoglobulin preparation as is known in the art, such as high-titered anti-HIV intravenous immunoglobulins.

Pharmaceutical compositions include suitable solutions for administration by injection, inhalation or by oral ingestion, and contain from about 0.01 to 99 percent, preferably from about 20 to 75 percent of active component (i.e. the antibody) together with the excipient. Pharmaceutical compositions for inhalation include sprays and inhalation mists. Pharmaceutical compositions for oral administration include tablets and capsules. Compositions which can be administered rectally, include suppositories.

In addition, the antibodies or combinations of antibodies of the present invention may be incorporated into agents which are used to contact fluids suspected of containing HIV, for example, in spermicidal preparations, condoms, blood collection bags or other containers used for obtaining or storing body fluids.

The mAbs of the present invention can be conjugated to cytotoxic agents and used as immunotoxins (see, for example, Till, M. et al., *Proc. Natl. Acad. Sci. USA* 86:1987–1991 (1989); Vitetta et al., *Science* 238:1098–1104 (1987)), or incorporated onto the surface of liposomes containing anti-HIV drugs or toxins to specifically target such drugs or toxins to infected cells. As used herein, the term "immunotoxin" refers to a conjugate of an antibody with one or more toxins, drugs, radionuclides, or cytotoxic agents. A toxic moiety can either be chemically conjugated to the antibody of the invention, or alternatively, can be ligated through recombinant DNA technology. In such a ligation, the DNA encoding the toxic protein or an active fragment thereof is ligated to the DNA encoding the entire, or a portion of, the mAb heavy chain, light chain, or both. Such genetic constructs and method for making them are known in the art. Among the toxins that may be conjugated to the antibodies of the present invention are ricin, diphtheria toxin, Pseudomonas toxin, tumor necrosis factor-alpha, and others known in the art.

In a typical treatment using the mAbs of the present invention as immunotoxins, the antibody is conjugated to a toxin such as ricin or Pseudomonas enterotoxin that, alone, is toxic to HIV-infected as well as uninfected cells. By coupling the cytotoxic agent to the antibody, a high level of toxic efficacy can be achieved in a highly localized manner, against the target cell to which the antibody has delivered the toxin, with a sparing of neighboring infected cells to which the antibody did not bind.

EXAMPLE I

MATERIAL AND METHODS

Subjects

Nine to $54 \times 10^6$ mononuclear cells, separated from the blood of 142 HIV-seropositive subjects on Ficoll-Hypaque were used in these experiments.

Establishment of EBV-Transformed Cell Lines and Heterohybridomas

The method for producing cell lines synthesizing human mAbs to HIV-1 was previously described (Gorny et al., supra). Briefly, mononuclear cells were incubated overnight with Epstein-Barr virus. Cyclosporin A (Sandoz, East Hanover, N.J.) was incorporated into the medium at 0.5 $\mu$g/ml for the first week after in vitro infection of the cells. Cells were cultured for 3–4 weeks in 96-well plates and the supernatants screened for antibodies as described below. Cells in positive wells were expanded and then fused with the SHM-D33 mouse x human heteromyeloma as previously described. Fused cells were cultured for 24 hr., whereupon, $1 \times 10^4$ mouse peritoneal cells were added as feeder cells and cultures were continued in the presence of hypoxanthine, aminopterin, thymidine and ouabain. After 2–3 weeks, all culture supernatants were again screened for specific antibodies and positive cultures expanded. Antibody-producing hybrid cells were cloned by limiting dilution.

Immunoassays

To screen for antibodies binding to gp120, 96-well Immulon-2 plates (Dynatech) were coated overnight at 4° C. with recombinant gp120 (rgp120) prepared in baculovirus (purchased from Repligen, Cambridge, Mass.). The rgp120 was added at a concentration of 0.5 $\mu$g/ml in coating buffer, pH 9.6. Culture supernatants were added to the coated wells and incubated for 90 min. at 37° C. After washing with PBS-Tween, the reaction was detected with alkaline phosphatase-labeled goat anti-human IgG antibodies (Zymed) at a dilution of 1:1000.

Binding of Antibody to rgp120

The ability of anti-gp120 mAbs to bind to rgp120 bound by various methods was tested. The proteins from either of two virus strains, rgp120$_{HTLV-IIIB}$ (purchased from Repligen) or rgp120$_{SF-2}$ (provided by Chiron Corporation, Albany, Calif.), were bound directly to Immulon-2 plates at concentrations ranging from 50 to 1000 ng/ml. In an alternate method, the rgp120 preparations were indirectly coated onto the plates. First, Concanavalin A (Con A, Sigma) at 2 mg/ml in PBS was allowed to bind to the plastic for 1 hr. at room temperature. After washing five times with PBS-Tween, the rgp120 preparation was added at the concentrations noted above. After 4 hr. at room temperature, the plates were washed and incubated with 15% fetal calf serum in culture medium overnight in order to block unsaturated Con A carbohydrate-binding sites. Human mAbs, at 10 $\mu$g/ml in PBS-Tween, were added to the plates. Antibody binding was detected with goat anti-human IgG antibody labeled with alkaline phosphatase. PBS-Tween containing 1% bovine serum albumin (BSA) was used as a negative control.

Blocking of gp120-CD4 Binding

To detect the ability of mAbs to block gp120-CD4 interactions, plates were coated with 0.1 $\mu$g/ml of murine anti-V3$_{HTLV-IIIB}$ antibodies (American Biotechnology) for 4 hr. at room temperature. After washing with TBS-BSA (0.05M Tris, 0.9% NaCl, 0.05% Tween-20 and 1% BSA), the plates were blocked with TBS-BSA overnight or at 4° C. In a separate tube, human mAbs at varying concentrations were mixed in equal volumes with recombinant CD4 (rCD4) produced in CHO cells (DuPont) at an initial concentration of 500 ng/ml and with rgp120$_{HTLV-IIIB}$ at an initial concentration of 1000 ng/ml. This "triplex" mixture was incubated for 2 hr. at 37° C. and then added to the coated plates. After 2 hr. at 37° C., the plates were washed and the presence of rCD4 was detected using alkaline phosphatase-labeled anti-CD4 mAb (ABT) at a dilution of 1:2000. This reaction was amplified with the GIBCO Immuno-select™ amplification system. This assay was designated as the "triplex" assay.

A second method, designated as the "duplex" assay, was used to measure the ability of mAbs to block CD4/gp120 interactions. Plates were coated with 0.1 $\mu$g murine anti-V3 IIIB antibodies (American Biotechnology) for 4 hr. at room temperature. After washing with TBS-BSA, plates were blocked with TBS-BSA at 4° C. overnight. After subsequent washing, rgp120$_{HTLV-IIIB}$ at a concentration of 1 $\mu$g/ml was added and incubated for 1.5 hr. at 37° C. After washing, 50 $\mu$l of varying concentrations of the human mAbs were added simultaneously with 50 $\mu$l of rCD4 at concentration of 500 $\mu$g/ml. This "duplex" mixture was incubated for 2 hr. at 37° C. After washing, the presence of rCD4 bound to the plate was detected using alkaline-phosphatase-conjugated anti-CD4 mAb (from American Biotechnology) at a dilution of 1:1500. This reaction was amplified with the GIBCO Immuno-select™ amplification system. The percentage of blocking of binding of rgp120 to rCD4 by the mAb was calculated using the formula: $100 \times (A_0 - A_+)/A_0$, wherein $A_0$ designates absorbance in the absence of added mAb and $A_+$ designates absorbance in the presence of added mAb.

Alternatively, to detect the presence of bound human IgG, alkaline phosphatase-labeled goat anti-human IgG was used. As a negative control, TBS-Tween containing 1% BSA replaced the human mAb.

Determination of Antibody Isotype

The antibody isotype was determined by ELISA. IgG was quantitated by methods previously described (Gorny, M. K. et al., *Proc. Nat'l. Acad. Sci. USA* 86:1624–1628 (1989)).

Radioimmunoprecipitation (RIP) Assays

RIP assays were carried out by the method of Pinter, A. et al. (*J. Immunol. Meth.* 112:735 (1988)) with 30 $\mu$g of HTLV-IIIB (Organon) or MN lysate (Advanced Biotechnologies, Silver Spring, Md.) labeled with $^{125}$I using the Bolton-Hunter reagent (New England Nuclear). Culture supernatants were incubated with labeled viral lysate and further processed for electrophoretic analysis as described (Gorny et al. (supra); Pinter et al., supra). When it was necessary to assess the dependence of antibody reactivity on antigen conformation, labeled viral lysate was reduced with 10 mM dithiothreitol and then alkylated with 11 mM iodoacetamide.

Western Blots

Western blot analyses were performed using kits purchased from Bio-Rad.

Measurement of Dissociation Constant (Kd)

Determination of the dissociation constants ($K_d$) of the binding of human mAbs was performed by an ELISA method according to Friguet et al., *J. Immunol. Methods* 77:305–319 (1985). Briefly, culture supernatants containing the mAbs were tested at concentrations ranging from 0.1 to 1.5 μg/ml. Rgp120 preparations in PBS (pH7.2) were used at concentrations ranging from $10^{-6}$ M to $10^{-9}$ M. Supernatant containing mAb and rgp120 were mixed in equal volumes, and, after 16 hr., the mixture was added to plates coated with the same species of rgp120 with which the mAb reacted. The amount of mAb not complexed with antigen in solution was measured by ELISA using alkaline phosphatase conjugated-antihuman IgG and the GIBCO Immunoselect™ amplification system. Data were plotted according to the Friguet modification of Klotz (Friguet et al., supra) to determine the $K_d$.

Virus Neutralization Assay

The syncytium forming infectivity assay of Nara, P. et al. (*AIDS Res. Hum. Retrovir.* 3:283–302 (1987)) was used to measure the neutralizing activity of the mAbs. This assay is based on the interaction between fusigenic virus-infected cells expressing the HIV envelope gene products and uninfected adjacent cells bearing CD4 molecules. It quantitates acute cell-free HIV-1 infection. Freshly prepared indicator cells (CEM-SS) in complete medium at $5 \times 10^4$ in 100 μl were plated onto poly-L-lysine coated microtiter wells. Serial two-fold dilutions of 100 μl of mAb preparation were incubated with 100 μl of filtered supernatant of chronically infected H9 cells, corresponding to 100–200 syncytial forming units (SFU), for 60 min. Duplicate wells of indicator cells were then exposed to 100 μl of the virus/antibody mixture for 1 hr. at 37° C. The supernatant containing antibody and free virus was then removed and the cells were washed with complete medium to remove free antibody or virus. Focal syncytium formation representing single infectious virus units was scored at day 5 by examination under an inverted microscope.

EXAMPLE II

Characterization of Human Monoclonal Antibodies Specific for the CD4-binding Domain of HIV gp120

EBV-transformed peripheral blood mononuclear cells from 142 patient specimens were screened for their ability to produce antibodies reactive with rgp120 coated directly on ELISA plates. On average, 1–2% of wells show positive reactivity on this initial screen. Of these, only four became stable lines after expansion, fusion and cloning. These four heterohybridomas each produced mAbs which were reactive with gp120$_{HTLV-IIIB}$ and gp120$_{MN}$ by radioimmunoprecipitation (RIP) (FIG. 1 and Table 1). However, only one of the four, 450-D, was reactive with gp120 from HTLV-IIIB on Western blot.

Further studies revealed that reduction and alkylation of viral lysates destroyed the ability of all but one of the mAbs, 450-D, to precipitate the gp120 (FIG. 1). This pattern was confirmed by ELISA reactivity with reduced and non-reduced rgp120 from HTLV-IIIB and SF-2. All four mAbs did not react with V3 loop peptides (19–22 mers) corresponding to eight different HIV-1 isolates. These results indicate that 450-D is reactive with an epitope present in both the native and the reduced form, while 448-D, 559/64-D and 588-D react only with an epitope present in native gp120. Specificity was nevertheless broad, since all four mAbs reacted with gp120 of three disparate HIV strains (MN, SF-2 and HTLV-IIIB).

TABLE 1

Characteristics of Human Monoclonal Antibodies Against gp120 HIV-1

| strain: Cell Line | Isotype | Specificity* | | Affinity (Kd = $10^{-8}$) for gp120 of | |
|---|---|---|---|---|---|
| | | RIP | WB | IIIB | SF-2 |
| 448-D | IgG1, lambda | gp120 | 0 | 2.9 | 0.5 |
| 559/64-D | IgG1, kappa | gp120 | 0 | 4.0 | 1.4 |
| 588-D | IgG1, kappa | gp120 | 0 | 2.0 | 0.6 |
| 450-D | IgG1, lambda | gp120 | gp120 | 7.5 | 1.5 |
| F105 | IgG1, kappa | | | 5.9 | 6.6 |
| 15e | IgG1, kappa | | | 12.0 | 7.5 |

*Specificity was tested by radioimmunoprecipitation (RIP) or Western blot (WB) using HTLV-IIIB.

The heavy chain isotype of all four the mAbs was IgG1. 448-D and 450-D had lambda light, whereas 559/64-D and 588-D had kappa light chains (Table 1). Dissociation constants (Kd) for the binding of each of the mAbs to rgp120$_{HTLV-IIIB}$ and to rgp120$_{SF-2}$ were determined. The Kd ranged from 0.5–7.5×$10^{-8}$ (Table 1). The $K_d$ was consistently lower, indicating higher affinity, for rgp120$_{SF-2}$, despite the fact that these mAbs were selected for their reactivity with rgp120$_{HTLV-IIIB}$. While this may reflect preferential specificity for SF-2 sequences, it is equally likely that this relates to differences associated with the source of the recombinant proteins (baculovirus for HTLV-IIIB and CHO cells for SF-2).

Analysis by ELISA revealed further differences in the reactivity and specificity of the mAbs. At 10 μg/ml, the mAbs reacted with as little as 50–100 ng/ml of rgp120 (FIGS. 2–5). The strength of the reaction was affected by the source of the rgp120 (baculovirus-derived HTLV-IIIB or CHO-derived SF-2) and the coating method used (direct or Con A-mediated). The differences in mAb reactivity with the various antigen preparations indicated that the epitope recognized by 448-D, 559/64-D and 588-D was optimally expressed on rgp120$_{HTLV-IIIB}$ coated to plastic via Con A. In contrast, 450-D reacted with an epitope optimally expressed on rgp120$_{SF-2}$ coated directly on the plastic.

The inability of these mAbs to react with gp120 V3 loop peptides, coupled with their binding to three disparate HIV-1 strains, suggested specificity for shared (i.e., group-specific) epitopes. To determine more precisely which region of gp120 these mAbs recognized, their ability to inhibit the binding of soluble CD4 to gp120 was tested.

Three mAbs, 448-D, 559/64-D and 588-D, inhibited CD4-rgp120 binding (Table 2). These were the antibodies which required native gp120 structure for binding. 450-D did not inhibit in this assay.

TABLE 2

Blocking of rCD4-rgp120 Binding by Human mAbs

| mAb | % Blocking in: | |
|---|---|---|
| | Duplex Assay | Triplex Assay |
| 448-D | 27 | 64 |
| 559/64-D | 23 | 45 |
| 588-D | 31 | 45 |
| F105 | 0 | 0 |
| 15e | 6 | 32 |

Starting concentration of mAbs was 5 µg/ml. In the Duplex assay, the final concentration is divided by two. In the Triplex assay, the final concentration is divided by three.

As previously noted, the CD4-binding domain of gp120 is a large conformation-dependent region on the surface of the molecule (Olshevsky et al., supra; Kowalski et al., supra). Thus, antibodies directed to this region, while specifically reactive to different, non-overlapping epitopes, may nevertheless prevent CD4/gp120 binding, inhibit virus infectivity and have comparable Kd values (see Table I). Nonetheless, due to their recognition of different epitopes, these mAbs could have different immunological and biological activities. Thus, human mAb 15e (Robinson J. E. et al., supra) neutralizes the IIIB and Z84 isolates of HIV-1, but does not neutralize RF and AL (Ho, D. D. et al. (1991), supra). In contrast, human mAb F105 (Posner M. R. et al., sudra) neutralizes MN but is only weakly effective against IIIB.

As noted above and shown in Table 2, mAbs 448-D, 559/64-D and 588-D can be distinguished from mAbs 15e and F105 on the basis of their ability to inhibit CD4/gp120 binding in the "duplex" assay. The distinction between the three mAbs of the present invention and those previously described by others is further confirmed by the results shown in FIG. 8. In this assay, rgp120 was bound to ELISA wells, and the ability of various mAbs (at 5 µg/ml) to inhibit the binding of the same or different biotin-labeled mAbs was tested. TBS or mAb 450-D, which binds to an epitope outside the CD4-binding domain, served as negative controls. In FIG. 8, panel A, is shown that mAb 448-D inhibited the binding of biotin-labeled 448-D. Similarly, this mAb inhibited the binding of biotin-labeled 559-D (panel B) and of biotin-labeled 588-D (panel C). However, neither mAb 15e nor F105 inhibited the binding of biotin-labeled 448-D, 559/64-D or 588-D. These results indicate that mAbs 448-D, 559/64-D and 588-D recognize an overlapping epitope or epitopes which are distinct from the epitopes recognized by either mAb 15e or mAb F105.

Figure 6:
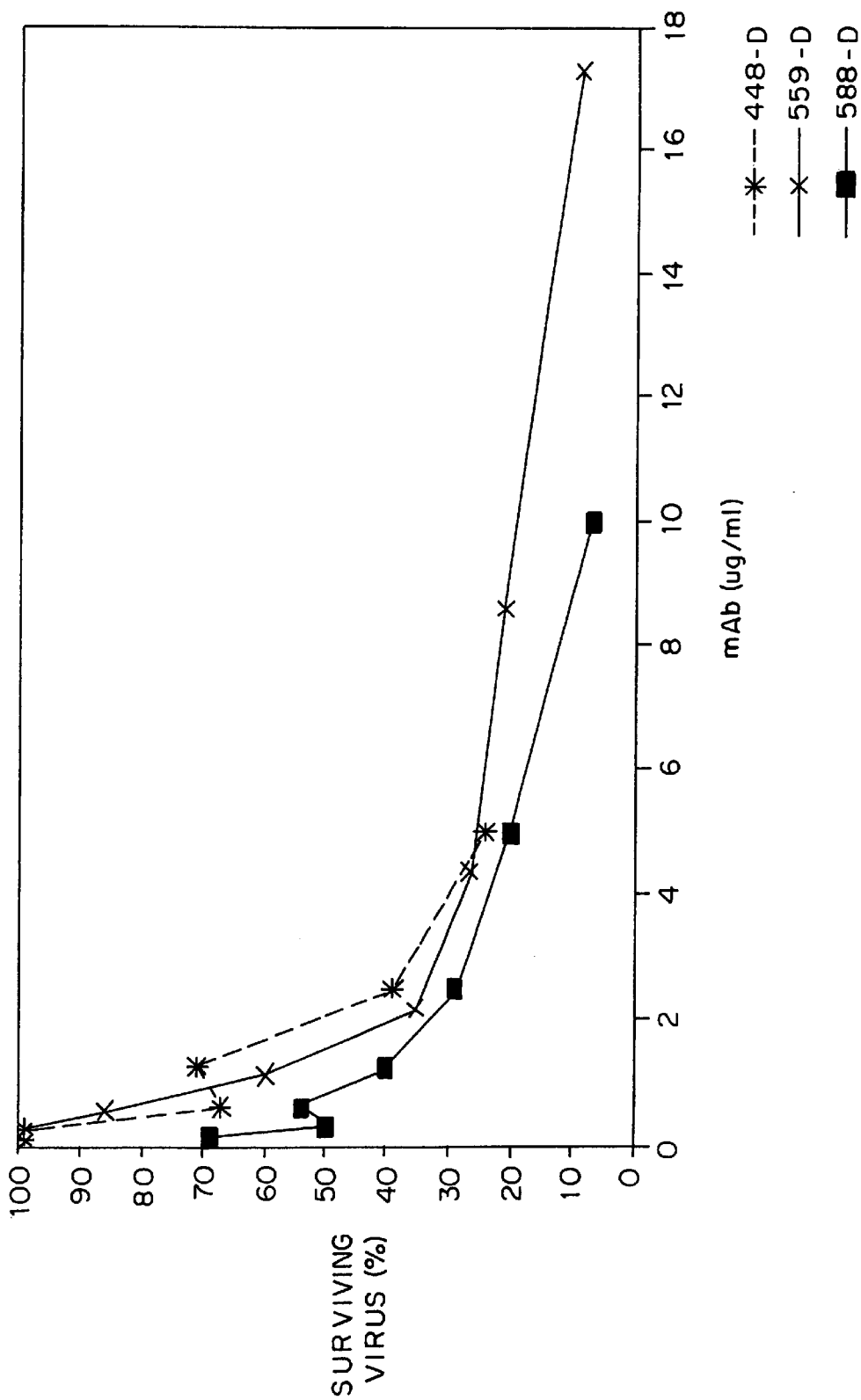
FIG. 6 is a graph showing neutralization of $HIV-1_{III-B}$ by various human mAbs.

Other studies have shown that other human mAbs specific for the gp120 CD4-binding domain neutralize virus (Robinson, J. et al., supra; Ho et al., supra; Posner et al., supra). The HIV-neutralization activity of the present mAbs was tested in a syncytium-forming infectivity assay. The three mAbs which are conformation-dependent and inhibit the interaction of CD4 and gp120 were able to neutralize both HTLV-IIIB and MN strains of virus. The 50% neutralizing dose ranged from 0.53 to 10.5 µg/ml, whereas the 90% neutralizing dose ranged from 7 to 188 µg/ml (Table 3). These values were calculated from experimental data using linear regression to generate a median effect equation (Chou T. et al., *Adv. Enz. Regul.* 22:27–55 (1984); Chou, J. et al., *Dose-effect Analysis with Microcomputers*, Biosoft, Cambridge, United Kingdom, 1987). Where R values of greater than 0.9 are obtained, the results are considered accurate for both 50% and 90% neutralization values. Where R values are less than 0.9, there is less confidence in the precision of the 90% neutralization values, which are considered precise only within one order of magnitude. 450-D, which reacted with denatured gp120 and could not block CD4-gp120 binding, did not significantly neutralize any of the virus strains tested. Representative dose response curves for the activity of mAbs 447-D, 559/64-D and 588-D against $HIV_{MN}$ and $HIV_{IIIB}$ are shown in FIGS. 6 and 7.

TABLE 3

Neutralizing Activity of Human Monoclonal Antibodies to the CD4-binding Domain of gp120*

| | Neutralizing Dose (µg IgG/ml) | | | |
|---|---|---|---|---|
| | HTLV-IIIB | | MN | |
| HumAb | 50% | 90% | 50% | 90% |
| 448-D | 3.72 | 188 | 2.07 | 7.02 |
| 559-/64D | 2.9 | 9.7 | 1.45 | 34.4 |
| 588-D | 0.53 | 11.2 | 0.94 | 29.2 |
| 450-D[+] | nt | | >>20 | |

*The values in this Table were obtained from the best fit curve using the data of Figures 6 and 7 with the program of Chou et al. (supra). The R values for the curves ranged from 0.84 to 0.96. For R values less than 0.9, the accuracy of the values in this table should be considered to be within one order of magnitude.
[+]Antibody 450-D did not neutralize MN even at concentrations of 20 µg/ml.

DISCUSSION

The three mAbs specific for the CD4-binding domain described above, 448-D, 559/64-D and 588-D, were identified using a screening technique designed to identify mAbs which are highly cross-reactive among HIV-1 strains. Thus, initial screens for reactivity were performed with $gp120_{HTLV-IIIB}$. Since the prevalence of this strain in North American patients is only about 0.5% (LaRosa et al., *Science* 249:932–935 (1990)), it was hypothesized that an antibody reactive with this strain would possess broad group-specificity. This hypothesis was confirmed by the results presented above, as all of the mAbs reacted comparably with HTLV-IIIB, MN and SF-2 strains.

These mAbs are distinguished by high affinity for rgp120 (Table 1) and by their ability to react with nanogram quantities of rgp120 in ELISA. All three mAbs mediated 50% virus neutralization of IIIB at 0.5–3.7 µg/ml. This potency is comparable to that of the mAb disclosed by J. E. Robinson et al. (*AIDS Res. Hum. Retrovir.* 6:567–579 (1990)), and is considerably greater than that of the mAb described by Posner et al. (supra).

Using the same virus neutralization assay, human mAbs to the gp120 V3 region of the MN strain induced 50% neutralization of $HIV-1_{MN}$ at concentrations as low as 0.05 µg/ml (see below). Thus, the difference in potency between the human mAbs specific for V3 and those specific for the CD4-binding domain can be as great as 75-fold. Since affinities and isotypes of both sets of mAbs (primarily IgG1 molecules) are comparable, the isotype and the affinity do not account for the difference in activity.

EXAMPLE III

SYNERGY BETWEEN HUMAN MONOCLONAL ANTIBODIES TO HIV EXTENDS THEIR EFFECTIVE BIOLOGIC ACTIVITY AGAINST HOMOLOGOUS AND DIVERGENT STRAINS

The present inventors performed experiments to determine if mAbs to different regions of gp120 could act in synergy to neutralize HIV rather than enhance its infectivity, as shown in the prior art (Robinson, W. E. Jr. et al., *Proc. Natl. Acad. Sci. (USA)* 87:3185–3189 (1990); Robinson W. E. Jr et al., *J. Virol.* 65:4169–4176 (1991)).

The human mAbs were produced by EBV transformation of peripheral blood mononuclear cells obtained from HIV-infected subjects followed by fusion with the SHM-D33 heteromyeloma (Gorny et al., supra). Human mAb 447-D was identified by its reactivity with a 23-mer from the $V3_{MN}$ loop (i.e., the V3 loop from the MN strain of HIV-1). 447-D recognizes the highly conserved GPGR sequence (actually a GPXR sequence) present in the V3 loop of many strains of HIV. Though specific for the V3 loop, 447-D is not entirely type-specific in that it is highly cross-reactive by ELISA with the V3 loop peptides of at least eight HIV-1 isolates, including MN, RF and HTLV-IIIB. Neutralization was assayed using a syncytium forming infectivity assay (Nara, P. et al., *AIDS Res. Hum. Retrovir.* 3:283–302 (1987)).

As shown in Table 4, neutralization of 50% and 90% of MN strain virus required 0.052 and 0.9 μg/ml of 447-D. Neutralization of 50% and 90% of HTLV-IIIB strain virus required and 1.8 and 178 μg/ml of 447-D.

TABLE 4

NEUTRALIZING DOSES OF ANTI-GP120 HUMAN MONOCLONAL ANTIBODIES

|  | MN | | HTLV-IIIB | |
|---|---|---|---|---|
|  | 50% | 90% | 50% | 90% |
| 447-D | 0.052* | 0.9 | 1.8 | 178.0 |
| 588-D | 0.9 | 29.2 | 0.53 | 11.2 |
| 447-D + 588-D | n.d. | n.d. | 0.28* | 2.95* |

*Final concentration (μg/ml) of each mAb as calculated from the data in Table 5 using the program developed by Chou and Chou (Chou, J. et al., infra).

Human mAb 588-D reacts with recombinant gp120 of HTLV-IIIB, and inhibits the binding of gp120 to soluble recombinant CD4. Neutralization of 50% and 90% of IIIB strain virus required 0.53 and 11.2 μg/ml of 558-D; neutralization of 50% and 90% of MN required 0.9 and 29.2 μg/ml of 588-D (Table 4).

Combinations of 447-D and 588-D were tested for synergy in the neutralization of HIV, and such synergy was found. For example, while neutralization of HTLV-IIIB required 178 μg/ml of 447-D and 11 μg/ml of 588-D, a 1:1 mixture of the two human mAbs yielded 90% neutralization at a concentration of 2.95 μg/ml each (Tables 4 and 5). This represents a 60-fold increase in potency for mAb 447-D and a 4-fold increase in potency for mAb 588-D.

TABLE 5

MEAN PERCENT NEUTRALIZATION OF HTLV-IIIB BY HUMAN MONOCLONAL ANTIBODIES ALONE AND IN COMBINATION*

| mAb 588-D | mAb 447-D (μg/ml) | | | | | | | | |
|---|---|---|---|---|---|---|---|---|---|
| (μg/ml) | 0 | .078 | .156 | .313 | .625 | 1.25 | 2.5 | 5.0 | 10.0 |
| 0 | 0 | — | 23 | 27 | 42 | 50 | 51 | 58 | 71 |
| 0.078 | — | 23 | | | | | | | |
| 0.156 | 31 | | 38 | | | | | | |
| 0.313 | 50 | | | 55 | | | | | |
| 0.625 | 46 | | | | 58 | | | | |
| 1.25 | 60 | | | | | 82 | | | |
| 2.5 | 71 | | | | | | 92 | | |
| 5.0 | 80 | | | | | | | 92 | |
| 10.0 | 93 | | | | | | | | — |

*Values represent percent neutralization as determined by the reduction of syncytia formation in the CEM-SS virus-induced syncytium-forming assay described by Nara (Nara, P. et al., AIDS Res. Hum. Retrovir. 3:283–302 (1987)). Values are shown for mAbs 447-D and 588-D alone, and in a 1:1 combination. CI for this combination show strong synergy (see text). Combinations of 1:3 and 3:1 of these mAbs show similar synergy in neutralizing activity. The R values measuring the mass-effect relationship were greater than 0.95 in all cases.

The "combination index" (CI) was calculated according to the method of Chou and Talalay (Chou T. et al., *Adv. Enz. Regul.* 22:27–55 (1984); Chou, J. et al., *Dose-effect Analysis with Microcomputers*, Biosoft, Cambridge, United Kingdom, 1987). Synergy is demonstrated when CI<1.0. The effect of 447-D and 588-D on neutralization of HTLV-IIIB was found to be highly synergistic. The combination index for 50% neutralization ($CI_{50\%}$) was 0.34 and the $CI_{90\%}$ was 0.14. This indicates that the combination was highly synergistic and not merely additive.

Synergy was also noted when using 3:1 or 1:3 mixtures of 447-D and 588-D, yielding a $CI_{90\%}$ of 0.12 in both cases. While this particular pair of anti-gp120 mAbs has been most extensively studied, other combinations of mAbs such as 447-D and 559-D, or 391-95D and 448-D, from the present inventors' laboratory, have similar synergistic activities.

These results while proving the existence of synergy between human mAbs in the neutralization of HIV, also have additional important implications. The present findings demonstrate that synergistic interactions-between two disparate antibodies effectively extend the "host range" and "efficacy" of a type-specific antibody. This can be illustrated as follows. The results presented above indicate that 90% neutralization of MN requires 0.9 μg/ml of 447-D. Similar neutralization of HTLV-IIIB requires 178.0 μg/ml. Thus, 447-D reacts with the V3 loop of MN more strongly than it does with the V3 loop of HTLV-IIIB in ELISA, reflected in its much weaker biologic (neutralizing) activity toward HTLV-IIIB. Nonetheless, by virtue of the synergy of 447-D with a different antibody (588-D) specific for the gp120 CD4-binding domain, 447-D in fact significantly gains in potency against the divergent strain (HTLV-IIIB). This, in effect, extends the biologic specificity and efficacy of 447-D.

These findings suggest that appropriate combinations of mAbs may provide a broader. spectrum of protection than expected on the basis of the activity of each antibody alone.

The mechanisms by which the two categories of gp120-specific human mAbs described above, anti-V3 and anti-CD4 binding domain, neutralize virus may explain their differential efficacy. Anti-V3 antibodies appear to prevent infection at a post-binding step (Nara, P., *Vaccines*, Cold Spring Harbor Press, Cold Spring Harbor, N.Y., 1989, pp. 137–144), possibly by preventing the cleavage of the V3 loop by a cell-associated protease (Clements, G. J. et al., *AIDS Res. Hum. Retrovir.* 7:3–16 (1991)). In contrast, anti-CD4-binding domain antibodies appear to prevent the virus binding to the cell surface. Thus, the anti-CD4-binding domain mAb's act as competitors for the CD4-gp120 binding reaction. To do so, antibodies, with a $K_d$ in the range of 0.5–7.5×10⁻⁸, must compete with a CD4-gp120 binding which has a $K_d$ of about $10^{-9}$M (Lasky, L. A. et al., *Cell* 50:975–985 (1987)), in an environment of a considerable molar excess of CD4 compared to antibody. This consideration may clarify the reason for the greater efficacy of anti-V3 antibodies.

Antibodies specific for the CD4-binding domain may be of particular importance in protecting against infection and in slowing disease progression by virtue of their recognition of a wide array (if not all) HIV-1 strains. The anti-V3 antibodies, while often cross-reactive, are generally more strain-specific or variant-specific. The synergy demonstrated above for these two classes of antibodies thus. serves to increase the potency of both and extend the effective biological activity of the anti-V3 class. It is therefore concluded that an optimal active HIV vaccine should stimulate both anti-V3 and anti-CD4-binding domain antibodies. Optimal passive immunotherapy should utilize a mixture of antibodies that have specificity at least for V3 and the CD4-binding domain.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

DEPOSITS

The following illustrative cell lines secreting human monoclonal antibodies specific for the CD4-binding domain of the gp120 protein of HIV-1 were deposited on Oct. 8, 1991, American Type Culture Collection, 12301 Parklawn Drive at the Rockville, Md. 20852, under the requirements for a U.S. Patent Deposit.

1. 448-D100,10,1 (also referred to as 448-D)
   Human×Human×Mouse Heterohybridoma cell line producing a human IgG1, lambda antibody (ATCC accession #HB 10895)
2. 559/64-D100,10,1 (also referred to as 559/64-D)
   Human×Human×Mouse Heterohybridoma cell line producing a human IgG1, kappa antibody (ATCC accession #HB 10893)
3. 588-D100,10,1 (also referred to as 588-D)
   Human×Human×Mouse Heterohybridoma cell line producing a human IgG1, kappa antibody (ATCC accession #HB 10894)

What is claimed is:

1. A molecule capable of binding to an epitope of the CD4-binding domain of HIV-1 gp120, comprising:
   (a) a human monoclonal antibody specific for an epitope of the CD4-binding domain of HIV-1 gp120, which antibody is group-specific, neutralizing, and capable of binding to gp120 when the gp120 is bound to an immobilized anti-V3 loop antibody, wherein said antibody has all the antigen binding characteristics of the human monoclonal antibody designated 448-D produced by the cell line having ATCC No. HB 10895, or
   (b) an antigen binding fragment of said human monoclonal antibody.

2. A molecule in accordance with claim 1, wherein said human monoclonal antibody is the antibody designated 448-D produced by the cell line having ATCC No. HB 10895.

3. A molecule in accordance with claim 1, wherein said molecule comprises said human monoclonal antibody of (a).

4. A molecule in accordance with claim 1, comprising said antigen binding fragment of (b).

5. A cell line producing a human monoclonal antibody according to claim 3.

6. A cell line in accordance with claim 5 which is a human-mouse heterohybridoma.

7. A cell line in accordance with claim 6 which is the cell line designated 448-D having ATCC No. HB 10895.

8. A method for neutralizing HIV-1 comprising contacting said HIV-1 with an effective amount of a molecule according to claim 1.

9. A method for decreasing the likelihood of infection by HIV-1 of a subject at risk for HIV-1 infection, or for treating a subject infected with HIV-1, comprising administering to said subject a therapeutically effective amount of a molecule according to claim 1.

10. A pharmaceutical composition comprising a molecule in accordance with claim 1 and a pharmaceutically acceptable excipient.

11. A molecule capable of binding to an epitope of the CD4-binding domain of HIV-1 qp120, comprising:
   (a) a human monoclonal antibody specific for an epitope of the CD4-binding domain of HIV-1 gp120, which antibody is group-specific, neutralizing, and capable of binding to gp120 when the gp120 is bound to an immobilized anti-V3 loop antibody, wherein said antibody has all the antigen binding characteristics of the human monoclonal antibody designated 559/64-D produced by the cell line having ATCC No. HB 10893, or
   (b) an antigen binding fragment of said human monoclonal antibody.

12. A molecule in accordance with claim 11, wherein said human monoclonal antibody is the antibody designated 559/64-D produced by the cell line having ATCC No. HB 10893.

13. A molecule in accordance with claim 11, wherein said molecule comprises said human monoclonal antibody of (a).

14. A molecule in accordance with claim 11, comprising said antigen binding fragment of (b).

15. A cell line producing a human monoclonal antibody according to claim 13.

16. A cell line in accordance with claim 15 which is a human-mouse heterohybridoma.

17. A cell line in accordance with claim 16 which is the cell line designated 559/64-D having ATCC No. HB 10893.

18. A method for neutralizing HIV-1 comprising contacting said HIV-1 with an effective amount of a molecule according to claim 11.

19. A method for decreasing the likelihood of infection by HIV-1 of a subject at risk for HIV-1 infection, or for treating a subject infected with HIV-1, comprising administering to said subject a therapeutically effective amount of a molecule according to claim 11.

20. A pharmaceutical composition comprising a molecule in accordance with claim 11 and a pharmaceutically acceptable excipient.

21. A molecule capable of binding to an epitope of the CD4-binding domain of HIV-1 gp120, comprising:

(a) a human monoclonal antibody specific for an epitope of the CD4-binding domain of HIV-1 gp120, which antibody is group-specific, neutralizing, and capable of binding to gp120 when the gp120 is bound to an immobilized anti-V3 loop antibody, wherein said antibody has all the antigen binding characteristics of the human monoclonal antibody designated 558-D produced by the cell line having ATCC No. HB 10894, or (b) an antigen binding fragment of said human monoclonal antibody.

22. A molecule in accordance with claim 21, wherein said human monoclonal antibody is the antibody designated 558-D produced by the cell line having ATCC No. HB 10894.

23. A molecule in accordance with claim 21, wherein said molecule comprises said human monoclonal antibody of (a).

24. A molecule in accordance with claim 21, comprising said antigen binding fragment of (b).

25. A cell line producing a human monoclonal antibody according to claim 23.

26. A cell line in accordance with claim 25 which is a human-mouse heterohybridoma.

27. A cell line in accordance with claim 26 which is the cell line designated 558-D having ATCC No. HB 10894.

28. A method for neutralizing HIV-1 comprising contacting said HIV-1 with an effective amount of a molecule according to claim 21.

29. A method for decreasing the likelihood of infection by HIV-1 of a subject at risk for HIV-1 infection, or for treating a subject infected with HIV-1, comprising administering to said subject a therapeutically effective amount of a molecule according to claim 21.

30. A pharmaceutical composition comprising a molecule in accordance with claim 21 and a pharmaceutically acceptable excipient.

31. A composition useful for neutralizing HIV-1, decreasing the likelihood of infection by HIV-1, or treating a subject infected with HIV-1, comprising a therapeutically effective amount of a mixture of at least a first and a second antibody specific for different epitopes of HIV-1 gp120, wherein (a) said first antibody is a molecule in accordance with claim 1; and (b) said second antibody is a molecule comprising an antibody or antigen binding fragment thereof specific for the V3 region, and has a range of neutralizing activity such that it neutralizes HIV-1 isolates MN, RF and IIIB, and wherein the neutralizing activity of said mixture is greater than the sum of the neutralizing activity of each antibody alone.

32. A method for neutralizing HIV-1 comprising contacting said HIV-1 with a composition according to claim 31, thereby neutralizing said HIV-1.

33. A method for decreasing the likelihood of infection by HIV-1 of a subject at risk for HIV-1 infection, or for treating a subject infected with HIV-1, comprising administering to said subject a therapeutically effective amount of a composition according to claim 31.

34. A pharmaceutical composition comprising the composition of claim 31 and a pharmaceutically acceptable excipient.

35. A composition useful for neutralizing HIV-1, decreasing the likelihood of infection by HIV-1, or treating a subject infected with HIV-1, comprising a therapeutically effective amount of a mixture of at least a first and a second antibody specific for different epitopes of HIV-1 gp120, wherein (a) said first antibody is a molecule in accordance with claim 11; and (b) said second antibody is a molecule comprising an antibody or antigen binding fragment thereof specific for the V3 region, and has a range of neutralizing activity such that it neutralizes HIV-1 isolates MN, RF and IIIB, and wherein the neutralizing activity of said mixture is greater than the sum of the neutralizing activity of each antibody alone.

36. A method for neutralizing HIV-1 comprising contacting said HIV-1 with a composition according to claim 35, thereby neutralizing said HIV-1.

37. A method for decreasing the likelihood of infection by HIV-1 of a subject at risk for HIV-1 infection, or for treating a subject infected with HIV-1, comprising administering to said subject a therapeutically effective amount of a composition according to claim 35.

38. A pharmaceutical composition comprising the composition of claim 35 and a pharmaceutically acceptable excipient.

39. A composition useful for neutralizing HIV-1, decreasing the likelihood of infection by HIV-1, or treating a subject infected with HIV-1, comprising a therapeutically effective amount of a mixture of at least a first and a second antibody specific for different epitopes of HIV-1 gp120, wherein (a) said first antibody is a molecule in accordance with claim 21; and (b) said second antibody is a molecule comprising an antibody or antigen binding fragment thereof specific for the V3 region, and has a range of neutralizing activity such that it neutralizes HIV-1 isolates MN, RF and IIIB, and wherein the neutralizing activity of said mixture is greater than the sum of the neutralizing activity of each antibody alone.

40. A method for neutralizing HIV-1 comprising contacting said HIV-1 with a composition according to claim 39, thereby neutralizing said HIV-1.

41. A method for decreasing the likelihood of infection by HIV-1 of a subject at risk for HIV-1 infection, or for treating a subject infected with HIV-1, comprising administering to said subject a therapeutically effective amount of a composition according to claim 39.

42. A pharmaceutical composition comprising the composition of claim 39 and a pharmaceutically acceptable excipient.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Gly Pro Gly Arg
      4

(2) INFORMATION FOR SEQ ID NO: 2:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 2:

Gly Pro Xaa Arg
      4

-continued (2) INFORMATION FOR SEQ ID NO: 3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Gly Pro Gly Xaa
          4

(2) INFORMATION FOR SEQ ID NO: 4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Gly Leu Gly Gln